US005541183A

United States Patent [19]
Park et al.

[11] Patent Number: 5,541,183
[45] Date of Patent: Jul. 30, 1996

[54] GINKGOLIDE DERIVATIVES

[75] Inventors: Pyeong-Uk Park, Seoul; Sungsoo Pyo, Kyungki-do; Suk-Kwan Lee, Anyang-si; Jin H. Sung, Seoul; Wie J. Kwak, Seoul; Hwa-Kun Park, Seoul; Yong-Baik Cho, Kyungki-do; Geun Ho Ryu, Kyungki-do; Taek S. Kim, Kyungki-do, all of Rep. of Korea

[73] Assignee: Sunkyong Industries Co., Ltd., Kyungki-do, Rep. of Korea

[21] Appl. No.: 366,594

[22] Filed: Dec. 29, 1994

[30] Foreign Application Priority Data

Dec. 31, 1993 [KR] Rep. of Korea ............ 93-31993

[51] Int. Cl.$^6$ ............ A61K 31/365; A61K 31/535; C07D 519/00
[52] U.S. Cl. ............ 514/232.8; 514/468; 544/153; 544/378; 546/174; 546/197; 546/284.1; 548/267.8; 548/526; 549/297
[58] Field of Search ............ 544/153; 546/270; 549/297; 514/232.8

[56] References Cited

PUBLICATIONS

E. Sybertz, et al., "Cardiac, Coronary and Peripheral Vascular Effects of Acetyl Glyceryl Ether Phosphoryl Choline in the Anesthetized Dog," *The Journal of Pharmacology and Experimental Therapeutics*, vol. 232, No. 1, Jan., 1985, pp. 156–162.

G. Camussi, "Potential Roll of Platelet–Activating Factor in Renal Pathophysiology," *Kidney International*, vol. 29, No. 2, Feb., 1986, pp. 469–477.

P. Bessin, "PAF–Acether and Leukotriene Participation in Acute Circulatory Shock," *Pharmacological Research Communications*, vol. 18 Supplement, Aug., 1986, pp. 139–150.

G. Plante, et al., "Hemodynamic Effects of PAF–Acether," *Pharmacological Research Communications*, vol. 18 Supplement, Aug., 1986, pp. 173–179.

J. Benveniste, et al., "A Role for PAF–Acether (Platelet–Activating Factor) in Platelet–Dependent Vascular Diseases?," *Circulation*, vol. 72, No. 4, Oct., 1985, pp. 713–717.

T. Kamitani, et al., "Mechanisms(s) of the Hypotensive Effect of Synthetic 1–O–Octadecyl–2–O–Acetyl–Glycero–3–Phosphorylcholine," *European Journal of Pharmacology*, vol. 98, Nos. ¾, (Mar. 1984) pp. 357–366.

G. Feuerstein, et al., "Prostaglandins, Leukotrienes, and Platelet–Activating Factor in Shock," *Annual Review of Pharmacology and Toxicology*, vol. 27, 1987, pp. 301–313.

M. L. Foegh, et al., "Prolongation of Cardiac Allograft Survival with BN 52021, a Specific Antagonist of Platelet–Activating Factor," *Transplantation*, vol. 42, No. 1, Jul., 1986, pp. 86–88.

R. Joseph, et al., "Sensitivity to PAF is Increased in Migraine Patients," *Thrombosis and Haemostasis*, vol. 57, No. 1, Feb. 1987, p. 125.

P. Barnes, et al., "PAF Closely Mimics Pathology of Asthma," *Trends in Pharmacological Sciences*, vol. 8, Aug. 1987, pp. 285–286.

K. F. Chung, et al., "PAF Antagonists: Their Potential Therapeutic Role in Asthma," *Drugs*, vol. 35, No. 2, Feb., 1988, pp. 93–103.

A. J. Lewis, et al., "The Effects of Antiallergic and Bronchodilator Drugs on Platelet–Activating Factor (PAF–Acether) Induced Bronchospasm and Platelet Aggregation," *Agents and Actions*, vol. 15, No. 5/6, Dec., 1984, pp. 636–642.

C. P. Page, et al., "Inflammatory Medicators of Asthma," *European Journal of Respiratory Diseases*, Supplement No. 144, vol. 68, 1986, pp. 163–189.

T. Nakamura, et al., "Platelet–Activating Factor in Late Asthmatic Response," *International Archives of Allergy and Applied Immunology*, vol. 82, 1987, pp. 57–61.

M. Sonnenblick, et al., "Body Positional Effect on Gas Exchange in Unilateral Pleural Effusion," *Chest*, vol. 83, No. 5, May, 1983, p. 784–786.

J. Bonnet, et al., "Dependency of the PAF–Acether Induced Bronchospasm on the Lipoxygenase Pathway in the Guinea–pig," *Prostaglandins*, vol. 26, No. 3, Sep., 1983, pp. 457–466.

T. Panetta, et al., "Effects of a Platelet Activating Factor Antagonist (BN 52021) on Free Fatty Acids, Diacylglycerols, Polyphosphoinositides and Blood Flow in the Gerbil Brain: Inhibition of Ischemia–Reperfusion Induced Cerebral Injury," *Biochemical and Biophysical Research Communications*, vol. 149, No. 2, Dec., 1987, pp. 580–587.

N. Bazan, "Arachidonic Acid in the Modulation of Excitable Membrane Function and at the Onset of Brain Damage," *Arachidonic Acid Metabolism in the Nervous System*, vol. 559, Jul. 1989, pp. 1–16.

P. Braquet, et al., "Perspectives in Platelet–Activating Factor Research," *Pharmacological Reviews*, vol. 39, No. 2, Jun., 1987, pp. 97–145.

(List continued on next page.)

*Primary Examiner*—Robert W. Ramsuer
*Attorney, Agent, or Firm*—Finnegan, Henderson, Farabow, Garrett and Dunner, L.L.P.

[57] ABSTRACT

The present invention is directed to new ginkgolide derivatives, which may be used for the prevention or treatment of various PAF-induced diseases, and the pharmaceutical uses of these derivatives. The present invention is also directed to a process for preparing these ginkgolide derivatives.

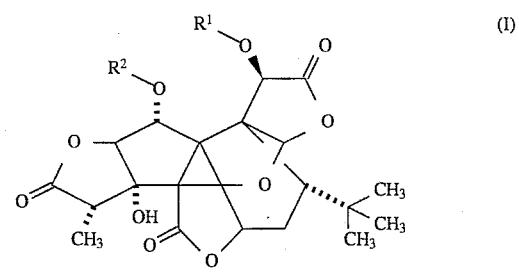

24 Claims, No Drawings

OTHER PUBLICATIONS

A. Rosam, et al., "Potent Ulcerogenic Actions of Platelet-Activating Factor on the Stomach," *Nature*, vol. 319, No. 6048, Jan., 1986, pp. 54–56.

A. Lefer, et al., "Pathophysiological Mechanisms of Sudden Death Induced by Platelet Activating Factor," *British Journal of Pharmacology*, vol. 83, No. 1, Sep., 1984, pp. 125–130.

A. Myers, et al., "Glucocorticoid Protection Against PAF-Acether Toxicity in Mice," *British Journal of Pharmacology*, vol. 79, No. 2, Jun., 1983, pp. 595–598.

M. Criscuoli, et al., "PAF–Acether–Induced Death in Mice: Involvement of Arachidonate Metabolites and β-Adrenoceptors," *British Journal of Pharmacology*, vol. 90, No. 1, Jan., 1987, pp. 203–209.

J. Young, et al., "Pharmacological Investigation of the Mechanisms of Platelet–Activating Factor Induced Mortality in the Mouse," *Prostaglandins*, vol. 30, No. 4, Oct., 1985, pp. 545–551.

P. Braquet, et al., "Platelet–Activating Factor and Cellular Immune Responses," *Immunology Today*, vol. 8, No. 11, 1987, pp. 345–352.

C. Caramelo, et al., "Increased Levels of Platelet–Activating Factor in Blood from Patients with Cirrhosis of the Liver," *European Journal of Clinical Investigation*, vol. 17, No. 1, Feb., 1987, pp. 7–11.

H. L. Spiegelberg, "Immunoglobins," *Imflammation: Basic Principles and Clinical Correlates*, Ch. 2 (1988), pp. 11–19.

A. Denjean, et al., "Bronchoconstriction Induced by Intratracheal Administration of Platelet–Activating Factor (PAF–Acether) in Baboons," *Agents and Actions*, vol. 11, Nos. 6/7, Dec. 1981, pp. 567–568.

N. Bazan, et al., "Platelet–Activating Factor and Polyunsaturated Fatty Acids in Cerebral Ischemia or Convulsions: Intracellular PAF–Binding Sites and Activation of a Fos/Jun./Ap–1 Transcriptional Signalling System," *Platelet–Activating Factor and Structurally Related Alkyl Ether Lipids*, vol. 26, No. 12 (1991), pp. 1236–1242.

G. Feuerstein, et al., "Effect of PAF on the Cardiovascular System," *Platelet–Activating Factor and Related Lipid Mediators*, Chap. 18, (1987) pp. 403–424.

F. Cuss, et al., "Effects of Inhaled Platelet Activating Factor on Pulmonary Function and Bronchial Responsiveness inf Man," *The Lancet*, vol. 13, No. 2 (1988), pp. 137–152.

D. Handley, "Development and Therapeutic Indications for PAF Receptor and Antagonists," *Drugs of the Future*, vol. 13, No. 2 (1988), pp. 137–152.

GINKGOLIDE DERIVATIVES

FIELD OF INVENTION

The present invention relates to new ginkgolide derivatives of formula (I), which have valuable PAF-antagonistic activity, and a process for preparing them, including a process for preparing Ginkgolide B derivatives and the pharmaceutical use of the derivatives. These compounds have excellent physiological activity.

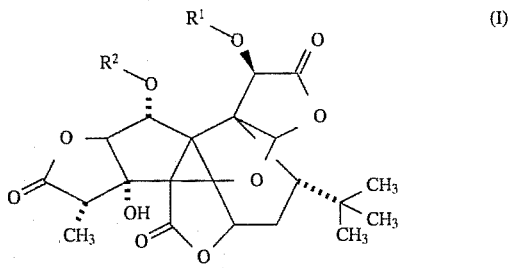

BACKGROUND OF THE INVENTION

Benveniste et al. found a factor in 1972 which strongly induced platelet aggregation from rabbit basophils. This factor was named platelet-activating factor (hereinafter referred to simply as PAF). Hanahan et al. identified the factor in 1980 as a phosphoglyceride of the alkyl ether type having an acetyl group in the 2-position, i.e. 1-O-hexadecyl or octadecyl-2-acetyl-sn-glyceryl-3-phosphorylcholine.

The physiological roles of PAF have been intensively investigated, and it is known that PAF is an important factor in various physiological reactions, including platelet aggregation, reduction in blood pressure, immediate allergic reaction, contraction of smooth muscle, inflammation, pain, edema, and alteration in the respiratory and circulatory systems.

Therefore, PAF-antagonistic activity-possessing compounds are very useful for treating various PAF-induced diseases, such as inflammatory diseases, allergic diseases, anaphylatic shocks, septic shocks, vascular diseases as DIC, myocardinal diseases, asthma, pulmonary edema, and adult respiratory diseases.

Compounds useful as therapeutic and prophylactic agents for cardiovascular diseases, such as, myocardial contiactility impairment, thrombocytopenia, hypotension, anaphylaxis shock or endotoxin shock are disclosed in J. Pharmacol. Exp. Ther., 1985, 232, 156; Kidney Int., 1986, 29, 469; Pharmacol. Res. Commun., 1986, 18(suppl), 139, 173; Circulation, 1985, 72, 713; Prostaglandins, Leukotrienes and Lipoxins, Plenum Press, New York, 1985, p.301; Eur. J. Pharmacol., 1984, 98, 357; Annu. Rev. Pharmacol. Toxicol., 1987, 27, 301; and Platelet-Activating Factor and Related Lipid Mediations, Plenum Press, New York, 1987, p.403. Compounds useful as therapeutic and prophylactic agents for organ transplantation are disclosed in Transplantation, 1986, 42, 86; Eur. J. Clin. Invest., 1987, 17, 7; and Thromb. Haemostasis, 1987, 57, 125. Compounds useful as therapeutic and prophylactic agents for inflammatory, edema and immunophathological conditions are disclosed in Inflammation-Basic Principles and Clinical Correlates, Raven Press, New York, 1988, p.13; Platelet-Activating Factor and Cell Immunology, Karger, Basel, 1988, vols 1 and 2; Drugs Future, 1988, 13, 137; and Immunol. Today, 1987, 8, 345. Compounds useful as therapeutic and prophylactic agents for asthma and respiratory conditions are disclosed in Trends Pharmacol. Sci., 1987, 8, 285; Drugs, 1988, 35, 93; Agents Actions, 1984, 15, 636; Eur. J. Respir. Dis., 1986, 68(suppl. 144), 163; Lancet, 1986, 2, 189; and Int. Arch. Allergy Appl. Immunol., 1987, 82, 57. Compounds useful as therapeutic and prophylactic agents for pulmonary hypertension and adult respiratory distress syndrome (ARDS) are disclosed in Chest, 1983, 83 (suppl.), 785; Agents Actions, 1981, 11, 567; and Prostaglandins, 1983, 26, 457. Compounds useful as therapeutic and prophylactic agents for ischemia are disclosed in Platelet-Activating Factor and Structurally Related Alkyl Ether Lipids, American Oil Chemist's Society, p.1236–1242, 1991; Biochem. Biophys. Res. Commun., 149, p.580–587, 1987; J. Neurochem., 151, p.88–109, 1988; Ann. N.Y. Acad. Sci., 559, p.1–16, 1989; and Pharmacol. Rev., 39, p.97–145, 987. Compounds useful as therapeutic and prophylactic agents for ulcergenesis and gastrointestinal alterations are disclosed in Nature (London), 1986, 319, 54. Compounds useful as therapeutic and prophylactic agents for lethal anaphylatic shock are disclosed in Br. J. Pharmacol., 1984, 83, 125; Br. J. Pharmacol., 1983, 79, 595; Br. J. Pharmacol., 1987, 90, 203; and Prostaglandins, 1985, 30, 545.

Under these circumstances, investigations have been made on compounds having anti-PAF activity. Among these compounds, ginkgolide compounds (A, B, C, M and J), which are terpenoid compounds from the roots and leaves of the Ginkgo tree, have exhibited the PAF antagonistic activity described above. However, these compounds possess certain deficiencies in the areas of effects on the central nervous system, potency, effectiveness by oral administration, water solubility, effectiveness by intravenous administration and duration of activity. Therefore, there is a need for potent PAF-antagonistic ginkgolide compounds which possess not only effectiveness by oral administration, long lasting effect, water solubility and effectiveness by intravenous administration, but also less inhibitory effects on the central nervous system.

Accordingly, the present inventors have conducted long term investigations and studies on ginkgolide derivatives which have not only excellent PAF-inhibiting activity, but also excellent physiological activity. The present invention has been accomplished based on these findings.

SUMMARY OF THE INVENTION

Accordingly, the present invention is directed to new ginkgolide derivatives, methods of preparing them and their pharmaceutical uses. Additional features and advantages of the invention will be set forth in the description which follows, and in part will be apparent from the description or may be learned from practice of the invention. The advantages of the invention will be realized and attained by the compounds and processes particularly pointed out in the written description and claims.

To achieve these and other advantages and in accordance with the purpose of the invention, as embodied and broadly described, the invention provides new ginkgolide derivatives, which may be used for the prevention or treatment of various PAF-induced diseases, and the pharmaceutical uses of these derivatives. There is also provided a process for preparing these ginkgolide derivatives.

It is to be understood that both the foregoing general description and the following detailed description are exemplary and explanatory and are intended to provide further explanation of the invention as claimed.

DETAILED DESCRIPTION OF THE INVENTION

The present invention relates to the new ginkgolide derivatives of the formula (I):

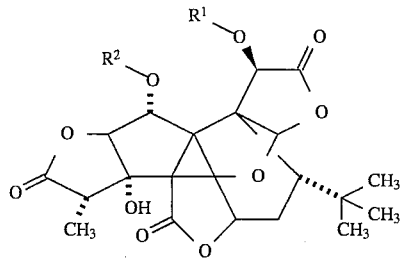

wherein
$R^2$ represents hydrogen or an $R^1$ group, and
$R^1$ represents —A—Ar, —A—Z—Ar,

—$SO_2$—Ar, —A—Het. or —A—$NR^4R^5$, in which

A represents an alkylene group having 1 to 8 carbon atoms, which is unsubstituted or substituted by a straight or branched alkyl chain having 1 to 5 carbon atoms, Z represents carbon, oxygen, sulfur or nitrogen, Ar represents a phenyl group, a pyridyl group, a naphthyl group, a pyrimidyl group, or a quinolyl group, each of which is unsubstituted or substituted by one to five substituents selected from the group consisting of hydrogen, a halogen atom, a hydroxy group, a carboxylic acid group, an alkyl group having 1 to 10 carbon atoms, an alkenyl group having 1 to 10 carbon atoms, an alkynyl group having 1 to 10 carbon atoms, a haloalkyl group having 1 to 10 carbon atoms, an alkoxy group having 1 to 10 carbon atoms, an alkenyloxy group having 1 to 10 carbon atoms, an alkynyloxy group having 1 to 10 carbon atoms, a haloalkoxy group having 1 to 10 carbon atoms, a phenyl group, a phenoxy group, an aralkyl group, an aralkyloxy group, a substituted phenyl group, a substituted phenoxy group, a substituted aralkyl group, a substituted aralkyloxy group, —$COR^4$, —$CONR^4R^5$, —$CO_2^{R4}$, —$NHCOR^4$, —$NH(OH)$, —$N(OH)COR^4$, —$CH_2OR^4$, —$OCH_2CO_2R^4$, —$CH_2SR^4$, —$CH_2NR^4R^5$, —$SR^4$, —$OSR^4$, —$SO_2NR^4R^5$, —$NR^4R^5$, —$NR^4SO_2R^5$ (in which $R^4$ and $R^5$ are the same or different and each is hydrogen, an alkyl group having 1 to 10 carbon atoms or a cycloalkyl group having 3 to 10 carbon atoms), —$SCX_3$ (in which X represents a halogen atom) —CN, —$NO_2$ and —Z—A—Z'— (in which Z and A are as defined above and Z' represents carbon, oxygen, sulfur, or nitrogen), Het. represents a cyclic saturated or unsaturated heterocyclic group having one or more nitrogen, oxygen, and/or sulfur atoms, and $R^4$ $R^5$ represent the same or different and each is hydrogen, an alkyl group having 1 to 10 carbon atoms or a cycloalkyl group having 3 to 10 carbon atoms.

Also, the present invention relates to the process for preparing the new ginkgolide derivatives of formula (I). The compounds of formula (I) can be prepared by reacting a compound of formula $R^1$-L and the known Ginkgolide B of formula (II) in the presence of bases and organic solvents.

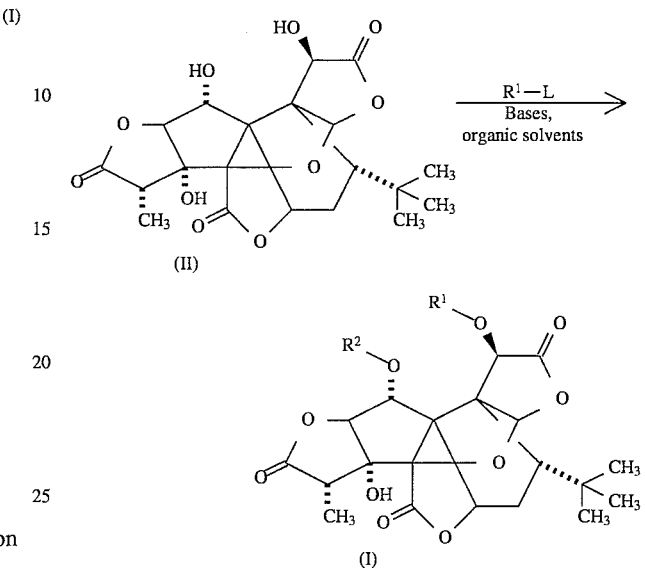

in the above reaction, $R^1$ and $R^2$ are as defined above, and L represents a halogen atom (for example, fluorine, chlorine, bromine or iodine), 4-metylbenzenesulfonyloxy, methanesulfonyloxy, 4-nifrobenzenesulfonyloxy, 4-bromobenzenesulfonyloxy or trifiuoromethanesulfonyloxy.

The present invention relates to the process for preparing the new ginkgolide derivatives of formula (I') by reacting a compound of formula (III) with a compound of formula Q-H.

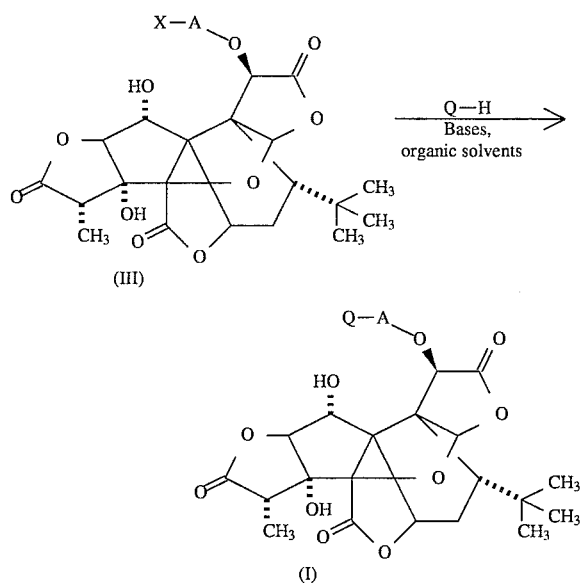

In the above reaction, A is as defined above, Q is Het. or $NR^4R^5$ (in which Het., $R^4$ and $R^5$ are as defined above), and X represents a halogen atom (fluorine, chlorine, bromine or iodine).

The compounds of the above formula (III) can be prepared by reacting a compound of formula (IV) and the known Ginkgolide B of formula (II) in the presence of bases and organic solvents.

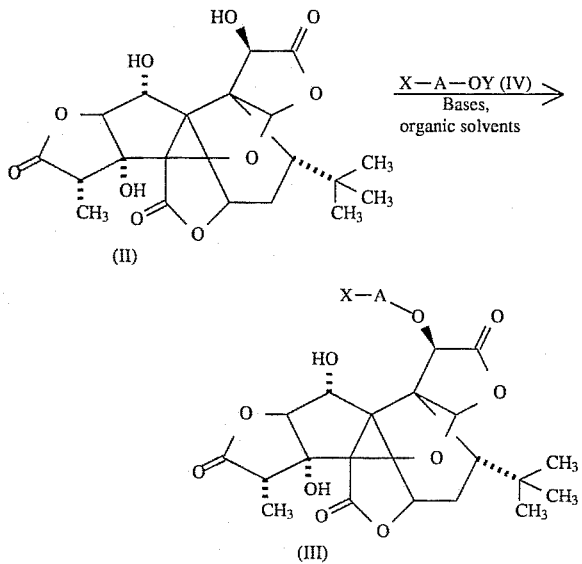

In the above reaction, X and A are as defined above, Y represents 4-methylbenzenesulfonyl, methanesulfonyl, 4-nitrobenzenesulfonyl, 4-bromobenzenesulfonyl, or trifluoromethanesulfonyl.

The detailed description of preferred embodiments of the present inventive compounds follows. Preferably, $R^1$ and $R^2$ in the above formula (I) are as shown below:

$R^2$ represents hydrogen or an $R^1$ group, and $R^1$ represents —A—Ar, —A—Z—Ar, —CO—Ar, —$SO_2$—Ar, —A—Het. or —A—$NR^4R^5$ in which A represents an alkylene group having 1 to 8 carbon atoms, for example, methylene, ethylene, trimethylene, tetramethylene, pentamethylene, hexamethylene, heptamethylene or octamethylene group, which is unsubstituted or substituted by a straight or branched chain alkyl group having 1 to 5 carbon atoms, such as methylmethylene, propylene, methyltrimethylene, dimethylethylene, dimetyltetramethylene, ethylethylene or dimethyltrimethylene; Z represents carbon, oxygen, sulfur or nitrogen; Ar represents a phenyl group, a pyridyl group (including, for example, 1-pyridyl, 2-pyridyl, 3-pyridyl and 4-pyridyl), a naphthyl group, a pyrimidyl group, or a quinolyl group, each of which is unsubstituted or substituted by one to five substituents; Het. represents a saturated or unsaturated heterocyclic group having one or more nitrogen, oxygen, and/or sulfur atoms, for example, morpholinyl, piperidinyl, piperazinyl, triazolyl, imidazolyl, pyrrolidyl, thiazolidinyl and furanyl.

In the above definitions, the term "substituents" in Ar includes hydrogen; halogen, including, for example, fluorine, chlorine, bromine or iodine; a hydroxy group; a carboxylic acid group; an alkyl group having 1 to 10 carbon atoms, including, for example, methyl, ethyl, n-propyl, isopropyl, n-butyl, isobutyl, tert-butyl, n-pentyl, isopentyl, 1-methylbutyl, n-hexyl, 1-methylpentyl, n-heptyl, 4-methylhexyl, 1-ethylpentyl, 1,4-dimethylpentyl, n-octyl, 6-methylheptyl or 2-ethylhexyl; an alkenyl group having 1 to 10 carbon atoms, including, for example, vinyl, allyl, 3-pentenyl or 1-hexenyl; an alkynyl group having 1 to 10 carbon atoms, including, for example, acetynyl group; a haloalkyl group having 1 to 10 carbon atoms, including, for example, fluoromethyl, chloromethyl, bromomethyl, iodomethyl, trifluoromethyl, trifluoroethyl, trifluoropropyl, trifluoromethylethyl or trifluoromethylpropyl; an alkoxy group having 1 to 10 carbon atoms, including, for example, methoxy, ethoxy, n-propoxy, isopropoxy, n-butoxy, isobutoxy, tert-butoxy, n-pentyloxy, isopentyloxy, n-hexyloxy, n-heptyloxy, 1-propylbutoxy, n-octyloxy, 5-methylhexyloxy, 2-ethylhexyloxy or 1,6-dimethylhexyloxy; an alkenyloxy group having 1 to 10 carbon atoms; an alkynyloxy group having 1 to 10 carbon atoms; a haloalkoxy group having 1 to 10 carbon atoms; a phenyl group; a phenoxy group; an aralkyl group, including, for example, benzyl, 1-phenylethyl, 2-phenylethyl, 3-phenylpropyl or 4-phenylbutyl; an aralkyloxy group, including, for example, benzyloxy, 2-phenylethoxy, 3-phenylpropoxy or 4-phenylbutoxy; a substituted phenyl group, including, for example, 2-chlorophenyl, 2-bromophenyl, 2-fluorophenyl, 2-iodophenyl, 3-fluorophenyl, 2,3-dichlorophenyl, 4-hydroxyphenyl, 2-methylphenyl, 4-methylphenyl, 3-ethylphenyl, 4-propylphenyl, 4-isopropylphenyl, 4-butylphenyl, 4-tert-butylphenyl, 4-pentylphenyl, 2,4-dimethylphenyl, 2-trifluoromethylphenyl, 3-trifluoromethylphenyl, 2-methoxyphenyl, 4-methoxyphenyl, 3-ethoxyphenyl, 2-propoxyphenyl, 4-butoxyphenyl or 2,4-dimethoxyphenyl; a substituted phenoxy group, including, for example, 3,4,5-trimethoxyphenoxy, 2-chlorophenoxy, 2,3-dichlorophenoxy, 4-hydroxyphenoxy, 2-methoxyphenoxy, 4-butylphenoxy or 2,4-dimethylphenoxy; a substituted aralkyl group, including, for example, chlorobenzyl, bromobenzyl, fluorobenzyl, iodobenzyl, dichlorobenzyl, dibromobenzyl, difluorobenzyl, hydroxybenzyl, methylbenzyl, halomethylbenzyl, methoxybenzyl or trimethoxybenzyl; a substituted aralkyloxy group, including, for example, chlorobenzyloxy, dimethylbenzyloxy, trifluoromethylbenzyloxy or trimethoxybenzyloxy; —$COR^4$; —$CONR^4R^5$; —$CO_2R^4$; $NHCOR^4$; —$N(OH)H$; —$N(OH)COR^4$; —$CH_2OR^4$; —$OCH_2CO_2R^4$; —$CH_2SR^4$; —$CH_2NR^4R^5$; —$SR^4$; —$OSR^4$; —$SO_2NR^4R^5$; —$NR^4R^5$; —$NR^4SO_2R^4$ (in which $R^4$ and $R^5$ are the same or different and each is hydrogen, an alkyl group having 1 to 10 carbon atoms or a cycloalkyl group having 3 to 10 carbon atoms); —$SCX_3$ (in which X represents halogen); —CN; —$NO_2$; or cyclic linked substituent, —Z—A—Z'— (in which, Z and A are as defined above and Z' represents carbon, oxygen, sulfur, or nitrogen), including, for example, —$OCH_2O$—, —$OCH_2CH_2O$—, —$OCH_2CH_2CH_2O$—, —$OCH_2CH_2N$—, —$NCH_2CH_2N$—, —$OCH_2CH_2$—, —$NCH_2CH_2$—, —$NCH_2CH_2CH_2$—, —$SCH_2S$—, —$SCH_2CH_2S$—, —$SCH_2$—, —$SCH_2CH_2$— or —$SCH_2CH_2CH_2$—.

Particularly preferred compounds of the present invention are the compounds of formula (I) wherein $R^2$ is hydrogen, and $R^1$ is —$CH_2$—Ar, —$CH_2$—$CH_2$—Ar, —$CH_2CH_2CH_2$—Ar, —$CH_2O$—Ar, —$CH_2CH_2O$—Ar, —$CH_2CH_2CH_2O$—Ar,

or —$SO_2$—Ar, in which Ar is a phenyl group, a pyridyl group, a pyrimidyl group, or a quinolyl group, each of which is unsubstituted or substituted by one to five substituents selected from the group consisting of hydrogen, halogen, a hydroxy group, an alkyl group having 1 to 10 carbon atoms, a haloalkyl group having 1 to 10 carbon atoms, an alkoxy group having 1 to 10 carbon atoms, a haloalkoxy group having 1 to 10 carbon atoms, a phenyl group, a phenoxy group, an aralkyl group, an aralkyloxy group,

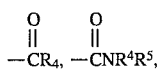

—$CO_2R^4$, —$CH_2OR^4$, —$NR^4R^5$, —$CH_2NR^4R^5$, —CN, —$NO_2$ and —Z—A—Z'—, wherein $R^4$, $R^5$, Z, A and Z' are as defined above.

More particularly preferred compounds of the present invention are the compounds selected from the group consisting of
10-benzyloxy-Ginkgolide B,
10-(2',4'-dichlorobenzyloxy)-Ginkgolide B,
10-(4'-chlorobenzyloxy)-Ginkgolide B,
10-(4'-methoxybenzyloxy)-Ginkgolide B,
10-(3',4',5'-trimethoxybenzyloxy)-Ginkgolide B,
10-(2'-methylbenzyloxy)-Ginkgolide B,
1,10-bis(2'-methylbenzyloxy)-Ginkgolide B,
10-(4'-methylbenzyloxy)-Ginkgolide B,
10-(3'-phenoxypropoxy)-Ginkgolide B,
10 -(2'-phenylethoxy)-Ginkgolide B,
10-(3',4',5'-trimethoxybenzoyloxy)-Ginkgolide B,
10-(4'-phenylbenzyloxy)-Ginkgolide B,
10-piperonyloxy-Ginkgolide B,
10-(2',3',4',5',6'-pentafluorobenzyloxy)-Ginkgolide B,
10-(2',4'-difluorobenzyloxy)-Ginkgolide B,
10-(4'-fluorobenzyloxy)-Ginkgolide B,
10-(2'-fluorobenzyloxy)-Ginkgolide B,
10-benzoyloxy-Ginkgolide B,
1-benzoyloxy-Ginkgolide B,
1,10-bis(2',4'-dichlorobenzyloxy)-Ginkgolide B,
10-(3'-trifluoromethylbenzyloxy)-Ginkgolide B,
10-benzenesulfonyloxy-Ginkgolide B,
10-(3'-methoxybenzyloxy)-Ginkgolide B,
10-(4'-trifluoromethylbenzyloxy)-Ginkgolide B,
1,10-bis(4'-trifluoromethylbenzyloxy)-Ginkgolide B,
10-(4'-hydroxybenzyloxy)-Ginkgolide B,
10-(4'-ethoxybenzyloxy)-Ginkgolide B,
10-(3'-bromobenzyloxy)-Ginkgolide B,
10-(4'-iodobenzyloxy)-Ginkgolide B,
10-(2',3',4'-trihydroxybenzyloxy)-Ginkgolide B,
10-(2'-iodobenzyloxy)-Ginkgolide B,
10-(2'-hydroxybenzyloxy)-Ginkgolide B,
10-(3'-iodobenzyloxy)-Ginkgolide B,
10-(3'-hydroxybenzyloxy)-Ginkgolide B,
10-(2'-bromobenzyloxy)-Ginkgolide B,
10-(3',4'-dihydroxybenzyloxy)-Ginkgolide B,
10-(4'-bromobenzyloxy)-Ginkgolide B,
10-(2'-chlorobenzyloxy)-Ginkgolide B,
10-(3'-chlorobenzyloxy)-Ginkgolide B,
10-(2',4',-dibromobenzyloxy)-Ginkgolide B,
10-(2',3',4',5',6'-pentachlorobenzloxy)-Ginkgolide B,
10-(2',3',4',5'-6'-pentabromobenzyloxy)-Ginkgolide B,
10-(2',3',4',5',6'-pentaiodobenzyloxy)-Ginkgolide B,
10-(2'-methoxybenzyloxy)-Ginkgolide B,
10-(3'-methoxybenzyloxy)-Ginkgolide B,
10-(2'-ethoxybenzyloxy)-Ginkgolide B,
10-(3'-ethoxybenzyloxy)-Ginkgolide B,
10-(2'-propoxybenzyloxy)-Ginkgolide B,
10-(3'-propoxybenzyloxy)-Ginkgolide B,
10-(4'-propoxybenzyloxy)-Ginkgolide B,
10-(2'-isopropoxybenzyloxy)-Ginkgolide B,
10-(3'-isopropoxybenzyloxy)-Ginkgolide B,
10-(4'-isopropoxybenzyloxy)-Ginkgolide B,
10-(4'-methlbenzyloxy)-Ginkgolide B,
10-(2'-ethylbenzyloxy)-Ginkgolide B,
10-(3'-ethylbenzyloxy)-Ginkgolide B,
10-(4'-ethylbenzyloxy)-Ginkgolide B,
10-(2'-propylbenzyloxy)-Ginkgolide B,
10-(3'-propylbenzyloxy)-Ginkgolide B,
10-(2'-bromoethoxy)-Ginkgolide B,
10-(2'-iodoethoxy)-Ginkgolide B,
10-(2'-(1"-piperidinyl)-ethoxy)-Ginkgolide B,
10-(2'-(1"-morphorinyl)-ethoxy)-Ginkgolide B,
10-(2'-(1"-(1", 2",4"-triazolyl)-ethoxy))-Ginkgolide B,
10-(2'-(1"-piperazinyl))-Ginkgolide B,
10- (2'-(1"-pyrrolidinyl)-ethoxy)-Ginkgolide B,
10-(3,5-dimethyl-2-pyridinyl)-methoxy-Ginkgolide B,
10-(4-methoxy-3,5-dimethyl-2-pyridinyl)-methoxy-Ginkgolide B,
10-(3,5-dimethyl-4-nitro-2-pyridinyl)-methoxy-Ginkgolide B,
10-(2-pyridinyl)-methoxy-Ginkgolide B,
10-(5-butyl-2-pyridinyl)-methoxy-Ginkgolide B,
10-(2-pyridinyl)-ethoxy-Ginkgolide B,
10-(2-quinolinyl)-methoxy-Ginkgolide B,
10-(3,5-dimethyl-4-amino-2-pyridinyl)-methoxy-Ginkgolide B,
10-(3,5-dimethyl-4-nifro-2-pyridnyl)-methoxy-Ginkgolide B,
10-(3,5-dimethyl-4-hydroxy-2-pyridinyl)-methoxy-Ginkgolide B,
10-(3,5-dimethyl-4-hydroxyamino-2-pyridinyl)-methoxy-Ginkgolide B,
10-(4-benzoylamino-3,5-dimethyl-2-pyridinyl)-methoxy-Ginkgolide B,
10-(4-N-benzoyl-N-hydroxyamino-3,5-dimethyl-2-pyridinyl-methoxy-Ginkgolide B,
10-(6-chloro-3-pyridinyl)-methoxy-Ginkgolide B,
10-(3-pyridinyl)-methoxy-Ginkgolide B,
10-(4-pyridinyl)-methoxy-Ginkgolide B,
10-(2-(4-ethoxypyridinyl))-methoxy-Ginkgolide B,
10-(2-(4-nitropyridinyl))-methoxy-Ginkgolide B,
10-(2-(6-methyl-3-propoxypyridinyl))-methoxy-Ginkgolide B,
10-(2-(4-hydroxyaminopyridinyl))-methoxy-Ginkgolide B,
10-(2-(5-methoxyethoxymethoxypyridinyl))-methoxy-Ginkgolide B,
10-(2-(5-hydroxypyridinyl))-methoxy-Ginkgolide B,
10-(4'-propylbenzyloxy)-Ginkgolide B,
10-(2'-isopropylbenzyloxy)-Ginkgolide B,
10-(3'-isopropylbenzyloxy)-Ginkgolide B,
10-(4'-isopropylbenzyloxy)-Ginkgolide B,
10-(2'-butylbenzyloxy)-Ginkgolide B,
10-(3'-butylbenzyloxy)-Ginkgolide B,
10-(4'-butylbenzyloxy)-Ginkgolide B,
10-(4'-pentylbenzyloxy)-Ginkgolide B,
10-(2',3'-dihydroxybenzyloxy)-Ginkgolide B,
10-(2',4'-dihydroxybenzyloxy)-Ginkgolide B,
10-(2',5'-dihydroxybenzyloxy)-Ginkgolide B,
10-(2',6'-dihydroxybenzyloxy)-Ginkgolide B,
10-(3',5'-dihydroxybenzyloxy)-Ginkgolide B,
10-(3-,6'-dihydroxybenzyloxy)-Ginkgoide B,
10-(3',4-,5'-trihydroxybenzyloxy)-Ginkgolide B,
10-(2'-vinylbenzyloxy)-Ginkgolide B,
10-(3'-vinylbenzyloxy)-Ginkgolide B,
10-(4'-vinylbenzyloxy)-Ginkgolide B,
10-(2'-allylbenzyloxy)-Ginkgolide B,
10-(2'-trifluoromethylbenzyloxy)-Ginkgolide B,
10-(2'-trichloromethylbenzyloxy)-Ginkgolide B,
10-(3'-trichloromethylbenzyloxy)-Ginkgolide B,
10-(4'-trichloromethylbenzyloxy)-Ginkgolide B,
10-(2'-tribromomethbenzyloxy)-Ginkgolide B,
10-(3'-tribromomethylbenzyloxy)-Ginkgolide B,
10-(4'-tribromomethylbenzyloxy)-Ginkgolide B, 10-(2'-fluoromethylbenzyloxy)-Ginkgolide B,
10-(3'-allylbenzyloxy)-Ginkgolide B,
10-(4'-allylbenzyloxy)-Ginkgohde B,
10-(3'-fluoromethylbenzyloxy)-Ginkgolide B,
10-(4'-fluoromethylbenzyloxy)-Ginkgolide B,
10-(2'-chloromethylbenzyloxy)-Ginkgolide B,
10-(3'-chloromethylbenzyloxy)-Ginkgolide B,
10-(4'-chloromethylbenzyloxy)-Ginkgolide B,
10-(2'-bromomethylbenzyloxy)-Ginkgolide B,
10-(3'-bromomethylbenzyloxy)-Ginkgolide B,
10-(4'-bromomethylbenzyloxy)-Ginkgolide B,
10-(2'-fluoromethoxybenzyloxy)-Ginkgolide B,
10-(3'-fluoromethoxybenzyloxy)-Ginkgolide B,
10-(4'-fluoromethoxybenzyloxy)-Ginkgolide B,
10-(2'-chloromethoxybenzyloxy)-Ginkgolide B,
10-(3'-chloromethoxybenzyloxy)-Ginkgolide B,
10-(4'-chloromethoxybenzyloxy)-Ginkgolide B,
10-(2'-bromomethoxybenzyloxy)-Ginkgolide B,
10-(3'-bromomethoxybenzyloxy)-Ginkgolide B,
10-(4'-bromomethoxybenzyloxy)-Ginkgolide B,
10-(2'-trifluoromethoxybenzyloxy)-Ginkgolide B,
10-(3'-trifluoromethoxybenzyloxy)-Ginkgolide B,
10-(4'-trifluoromethoxybenzyloxy)-Ginkgolide B,
10-(2'-trichloromethoxybenzyloxy)-Ginkgolide B,
10-(3'-trichloromethoxybenzyloxy)-Ginkgolide B,
10-(4'-trichloromethoxybenzyloxy)-Ginkgolide B,
10-(2'-tribromomethoxybenzyloxy)-Ginkgolide B,
10-(3'-tribromomethoxybenzyloxy)-Ginkgolide B,
10-(4'-tribromomethoxybenzyloxy)-Ginkgolide B,
10-(2'-phenoxybenzyloxy)-Ginkgolide B,
10-(2'-benzylbenzyloxy)-Ginkgolide B,
10-(3'-phenoxybenzyloxy)-Ginkgolide B,
10-(3'-benzylbenzyloxy)-Ginkgolide B,
10-(4'-phenoxybenzyloxy)-Ginkgolide B,
10-(4'-benzylbenzyloxy)-Ginkgolide B,
10-(1'-phenethoxy)-Ginkgolide B,
10-(3'-phenpropoxy)-Ginkgolide B,
10-(4'-phenbutoxy)-Ginkgolide B,
10-(4'-(2"-phenethyl)-benzyloxy)-Ginkgolide B,
10-(4'-(1"-phenethyl)-benzyloxy)-Ginkgolide B,
10-(4'-(3"-phenpropyl)-benzyloxy)-Ginkgohde B,
10-(4'-(4"-phenbutyl)-benzyloxy)-Ginkgolide B,
10-(4'-(2"-chlorophenyl)-benzyloxy)-Ginkgolide B,
10-(4'-(2"-bromophenyl)-benzyloxy)-Ginkgolide B,
10-(4'-(2"-fluorophenyl)-benzyloxy)-Ginkgolide B,
10-(4'-(2"-bromophenyl)-benzyloxy)-Ginkgolide B,
10-(4'-(2"-iodophenyl)-benzyloxy)-Ginkgolide B,
10-(4'-(3"-fluorophenyl)-benzyloxy)-Ginkgolide B,
10-(4'-(2",3"-dichlorophenyl)-benzyloxy)-Ginkgolide B,
10-(4'-(4"-hydroxyphenyl)-benzyloxy)-Ginkgolide B,
10-(4'-(2"-methylphenyl)-benzyloxy)-Ginkgolide B,
10-(4'-(4"-methylphenyl)-benzyloxy)-Ginkgolide B,
10-(4'-(3"-ethylphenyl)-benzyloxy)-Ginkgolide B,
10-(4'-(4"-propylphenyl)-benzyloxy)-Ginkgolide B,
10-(4'-(4"-isopropylphenyl)-benzyloxy)-Ginkgolide B,
10-(4'-(4"-butylphenyl)-benzyloxy)-Ginkgolide B,
10-(4'-(4"-pentylphenyl)-benzyloxy)-Ginkgolide B,
10-(4'-(2",4"-dimethylphenyl)-benzyloxy)-Ginkgolide B,
10-(4'-(2"-trifluoromethylphenyl)-benzyloxy)-Ginkgolide B,
10-(4'-(2"-methoxyphenyl)-benzyloxy)-Ginkgolide B,
10-(4'-(3"-methoxyphenyl)-benzyloxy)-Ginkgolide B,
10-(4'-(4"-methoxyphenyl)-benzyloxy)-Ginkgolide B,
10-(4'-(3"-ethoxyphenyl)-benzyloxy)-Ginkgolide B,
10-(4'-(2"-propoxyphenyl)-benzyloxy)-Ginkgolide B,
10-(4'-(4"-butoxyphenyl)-benzyloxy)-Ginkgolide B,
10-(4'-(2",4"-dimethoxyphenyl)-benzyloxy)-Ginkgolide B,
10-(4'-(3",4",5"-trimethoxyphenoxy)-benzyloxy)-Ginkgolide B,
10-(4'-(2"-chlorophenoxy)-benzyloxy)-Ginkgolide B,
10-(4'-(2",3"-dichlorophenoxy)-benzyloxy)-Ginkgolide B,
10-(4'-(4"-hydroxyphenoxy)-benzyloxy)- Ginkgolide B,
10-(4'-(2"-methoxyphenoxy)-benzyloxy)-Ginkgolide B,
10-(4'-(4"-butylphenoxy)-.benzyloxy)-Ginkgolide B,
10-(4'-(2",4"-dimethylphenoxy)-benzyloxy)-Ginkgohde B,
10-(4'-(4"-chlorobenzyl)-benzyloxy)-Ginkgolide B,
10-(4'-(4"-bromobenzyl)-benzyloxy)-Ginkgolide B,
10-(4'-(4"-fluorobenzyl)-benzyloxy)-Ginkgolide B,
10-(2'-nitrobenzyloxy)-Ginkgolide B,
10-(3'-nitrobenzyloxy)-Ginkgolide B,
10-(4'-nitrobenzyloxy)-Ginkgolide B,
10-(2'-cyanobenzyloxy)-Ginkgolide B,
10-(3'-cyanobenzyloxy)-Ginkgolide B,
10-(4'-cyanobenzyloxy)-Ginkgolide B,
10-(2'-aminobenzyloxy)-Ginkgolide B,
10-(3'-aminobenzyloxy)-Ginkgolide B,
10-(4'-aminobenzyloxy)-Ginkgolide B,
10-(2'-dimethylaminobenzyloxy)-Ginkgolide B,
10-(3'-dimethylaminobenzyloxy)-Ginkgolide B,
10-(4'-dimethylaminobenzyloxy)-Ginkgolide B,
10-(3',4'-dihydroxybenzyloxy)-Ginkgolide B,
10-(3,5-dimethyl-4-hydroxybenzyloxy)-Ginkgolide B,
10-(3,5-di-tert-butyl-4-hydroxybenzyloxy)-Ginkgolide B,
10-(4-hydroxy-3-methoxybenzyloxy)-Ginkgolide B,
10-(3,5-dimethoxy-4-hydroxybenzyloxy)-Ginkgolide B and
10-(3-amino-4-hydroxy-5-methyl-benzyloxy)-Ginkgolide B.

The present invention further provides the pharmacological use of the compound of formula (I) defined above. According to the present invention, a pharmaceutical composition is provided which comprises a pharmacologically effective amount of a compound of formula (I) and a pharmacologically acceptable carrier.

The present invention also provides a method for treating a disease against which anti-PAF activity is effective, which comprises administering a pharmacologically effective amount of a compound of formula (I) to a host in need. The diseases which may be treated in this manner include allergic diseases such as asthma, inflammatory diseases, septic shock and anaphylactic shock, vascular diseases such as DIC, myocardial diseases, pulmonary edema and adult respiratory diseases.

To prepare compounds of the formula (I), the compounds of formula (II) defined above may be reacted with a compound of formula $R^1$-L defined above.

This reaction is usually carried out for 1 to 10 hours at 0°–70° C. in a solvent (e.g., tetrahydrofuran, acetone, ethyl acetate, dimethyl formamide, dimethyl sulfoxide, pyridine, dioxane, methanol, ethanol, 2-methoxyethanol or a mixed solvent thereof) in the presence of an easily available base.

These easily available bases include, for example, $Ag_2O$, triethylamine, an alkalicarbonate, an alkalibicarbonate, an alkali hydroxide, MH, wherein M is alkali metal such as Li, Na, K, etc. (e.g., lithium hydride, sodium hydride, potassium hydride), $MNH_2$ (e.g., sodium amide, etc.), $MOR_4$, $MR^4$, $R^4R^5NM$, $MN(TMS)_2$ and mixtures thereof ($R^4$ and $R^5$ are the same as defined above and TMS is trimethylsilyl group).

Also, for preparing compounds of formula (I'), compounds of formula (III) defined above may be reacted with with a compound of formula Q-H defined above either in the presence of solvent and base or in the absence of solvent and base.

In the above reaction, the reaction is usually carried out for 1 to 10 hours at 0°–90° C. in a solvent (e.g., tetrahydrofuran, acetone, ethyl acetate, dimethyl formamide, dimethyl sulfoxide, pyridine, dioxane, methanol, 2-methoxyethanol or mixtures thereof) in the presence of an easily available base (as defined above).

The compounds of the formula (I') may also be prepared from the compounds of the formula (III) and Q-H directly, i.e. in the absence of solvent and base. In this reaction, it is especially preferable to conduct the reaction at 0°–90° C. due to the slowness of the reaction below 0° C. and the presence of side reactions above 90° C., which result in low yields.

Also, compounds of formula (III) may be prepared by reacting a compound of formula (II) and a compound of formula (IV) in a mixed organic solvent (as defined above) in the presence of an easily available base for 1 to 10 hours at 0°–90° C. In this reaction, the organic solvent and base are the same as employed in the preparation of compounds of the formula (I) described above.

In accordance with the present invention, from study of the structure-activity relationship of Ginkgolide derivatives having substituents at the C-1 and/or C-10 position, the new Ginkgolide B derivative is useful as a PAF-antagonistic agent.

The following examples more fully illustrate the present invention, but the invention is not intended to be limited thereby.

Example 1. 10-benzyloxy-Ginkgolide B

To a solution of 50 mg of Ginkgolide B in 5 ml of tetrahydrofuran was added 16 mg of potassium hydride followed by stirring, in an inert atmosphere, at room temperature for 5 minutes. To the mixture was then added 60 mg of benzylbromide, followed by stirring at room temperature for 4 hours. The mixture was treated with 0.5 ml of c-HCl at 0° C., diluted with 10 ml of water and extracted with 50 ml of ethylacetate. The solution was washed with 10 ml of water and dried over anhydrous magnesium sulfate.

After filtering off, the filtrate was concentrated under reduced pressure. The residue was subjected to chromatography on silica gel (elution solvent: chloroform/methanol= 99/1) to give 51 mg (85%) of the desired compound.

$^1$H-NMR (CDCl$_3$); δ 7.38–7.31 (m, 5H), 6.44 (s, 1H), 6.16 (s, 1H), 5.32 (brs, 1H), 5.25 (s, 1H), 5.02 (ABq, 2H, J=11.4Hz, Δυ=193 Hz), 4.71 (d, 1H, J=4.5 Hz), 4.60(d, 1H, J=6.9 Hz), 4.17(dd, 1H, J=6.9, 4.5 Hz), 2.87 (q, 1H, J=6.9 Hz), 2.14 (dd, 1H, J=13.5 Hz, 3.6 Hz), 1.86(td, 1H), 1.75(dd, 1H), 1.12 (d, 1H, J=6.9 Hz), 1.02 (s, 9H).

Example 2. 10-(2',4'-dichlorobenzyloxy)-Ginkgolide B

To a solution of 50 mg of Ginkgolide B in 5 ml of tetrahydrofuran was added 16 mg of potassium hydride followed by stirring, in an inert atmosphere, at room temperature for 5 minutes.

To the mixture was then added 118 mg of 2,4-dichlorobenzyl iodide, followed by stirring at room temperature for 4 hours.

The mixture was treated with 0.5 ml of c-HCl at 0° C., diluted with 10 ml of water and extracted with 50 ml of ethylacetate. The solution was washed with 10 ml of water and dried over anhydrous magnesium sulfate.

After filtering off, the filtrate was concentrated under reduced pressure. The residue was subjected to chromatography on silica gel (elution solvent: chloroform/methanol= 99/1) to give 43 mg (62%) of the desired compound.

$^1$H-NMR (CDCl$_3$); δ 7.47–7.33(m, 3H), 5.99(5, 1H), 5.35(brs, 1H), 5.19 (ABq, 2H, J=9.9, Δυ=183 Hz), 4.90(s, 1H), 4.54(d, 1H, J=7.8 Hz), 4.24(dd, 1H, J=7.8, 2.4 Hz), 3.04 (q, 1H, J=6.9 Hz), 2.91(s, 1H), 2.75(d, 1H, J=2.4 Hz), 2.28(m, 1H), 1.95–1.92 (m, 2H), 1.30 (d, 3H, J=6.9 Hz), 1.11 (s, 9H).

Example 3. 10-(4'-chlorobenzyloxy)-Ginkgolide B

To a solution of 50 mg of Ginkgolide B in 5 ml of tetrahydrofuran was added 16 mg of potassium hydride followed by stirring, in an inert atmosphere, at room temperature for 5 minutes. To the mixture was then added 104 mg of 4-chlorobenzyliodide, followed by stirring at room temperature for 4 hours.

The mixture was treated with 0.5 ml of c-HCl at ° C., diluted with 10 ml of water and extracted with 50 ml of ethylacetate. The solution was washed with 10 ml of water and dried over anhydrous magnesium sulfate. After filtering off, the filtrate was concentrated under reduced pressure. The residue was subjected to chromatography on silica gel (elution solvent: chloroform/methanol =99/1) to give 47 mg (72%) of the desired compound.

$^1$H-NMR (CDCl$_3$); δ 7.42–7.39(m, 2H), 7.32–7.29(m, 2H), 5.99 (s, 1H), 5.32 (brs, 1H), 5.03 (ABq, 2H, J=9.6, Δυ=270 Hz), 4.90 (s, 1H), 4.54 (d, 1H, J=7.8 Hz), 4.27 (brs, 1H), 3.04 (q, 1H, J=6.6 Hz), 2.94 (brs, 1H), 2.75 (brs, 1H), 2.28 (1H), 1.90 (m, 2H), 1.28 (d, 3H), 1.14 (s, 9H).

Examples 4 to 13.

In the same manner as in Example 3, the following compounds were prepared.

| Example | R$^1$ | R$^2$ | m.p. (°C.) |
|---|---|---|---|
| 4 | 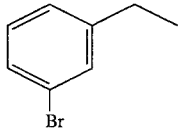 | H | 145–147 |
| 5 | 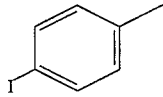 | H | |
| 6 | 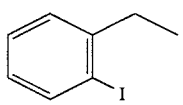 | H | |
| 7 | 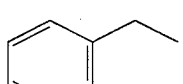 | H | |
| 8 | 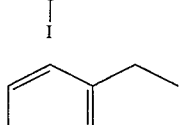 | H | |

-continued

| Example | R¹ | R² | m.p. (°C.) |
|---------|-----|-----|------------|
| 9 | 4-Br-benzyl | H | |
| 10 | 2-Cl-benzyl | H | |
| 11 | 3,4-diCl-benzyl | H | |
| 12 | 2,4-diBr-benzyl | H | 152.1~153.2 |
| 13 | 2,3,4,5,6-pentaBr-benzyl | H | |

Example 14. 10-(4'-methoxybenzyloxy)-Ginkgolide B

To a solution of 50 mg of Ginkgolide B in 5 ml of tetrahydrofuran was added 16 mg of potassium hydride followed by stirring, in an inert atmosphere, at room temperature for 5 minutes. To the mixture was then added 102 mg of 4-methoxybenzyl iodide, followed by stirring at room temperature for 4 hours.

The mixture was treated with 0.5 ml of c-HCl at 0° C., diluted with 10 ml of water and extracted with 50 ml of ethylacetate. The solution was washed with 10 ml of water and dried over anhydrous magnesium sulfate. After filtering off, the filtrate was concentrated under reduced pressure. The residue was subjected to chromatography on silica gel (elution solvent: chloroform/methanol =99/1) to give 53 mg (82%) of the desired compound.

$^1$H-NMR (CDCl$_3$); δ 7.30–7.26(m, 2H), 6.98–6.88(m, 2H), 5.98(s, 1H), 5.30(brs, 1H), 4.95(ABq, 2H, J=9.6 Hz, Δυ=264 Hz), 4.52 (d, 1H, J=7.8 Hz), 4.26 (dd, 1H, J=7.8, 3.3 Hz), 3.80 (d, 3H, J=1.5 Hz), 3.05 (q, 1H, J=7.2 Hz), 2.86 (d, 1H, J=3.3 Hz), 2.26 (m, 1H), 1.92–1.89 (m, 2H), 1.29 (d, 3H), 1.14 (s, 9H).

Example 15. 10-(3',4',5'-trimethoxybenzyloxy)-Ginkgolide B

To a solution of 50 mg of Ginkgolide B in 5 ml of tetrahydrofuran was added 16 mg of potassium hydride followed by stirring, in an inert atmosphere, at room temperature for 5 minutes. To the mixture was then added 127 mg of 3,4,5-trimethoxybenzyl iodide, followed by stirring at room temperature for 4 hours.

The mixture was treated with 0.5 ml of c-HCl at 0° C., diluted with 10 ml of water and extracted with 50 ml of ethylacetate. The solution was washed with 10 ml of water and dried over anhydrous magnesium sulfate. After filtering off, the filtrate was concentrated under reduced pressure. The residue was subjected to chromatography on silica gel (elution solvent: chloroform/methanol =99/1) to give 48 mg (68%) of the desired compound.

$^1$H-NMR (CDCl$_3$); δ 6.55 (s, 2H), 6.00 (s, 1H), 5.34 (brs, 1H), 4.99(ABq, 2H, J=9.3 Hz, Δυ=277 Hz), 4.89 (s, 1H), 4.56 (d, 1H, J=7.8 Hz), 3.95 (dd, 1H, J=7.8, 3.0 Hz), 3.87 (d, 9H), 3.06 (q, 1H, J=7.2 Hz), 2.85 (m, 1H), 2.0 . 1.80 (m, 2H), 1.31 (d, 3H, J=7.2 Hz), 1.14 (s, 9H).

Examples 16 to 40.

In the same manner as in Example 15, the following compounds were prepared.

| Example | R¹ | R² | m.p. (°C.) |
|---------|-----|-----|------------|
| 16 | 3-OC$_2$H$_5$-benzyl | H | 157.2~158.4 |
| 17 | 2-O-n-Pr-benzyl | H | |
| 18 | 3-O-n-Pr-benzyl | H | |
| 19 | 4-O-n-Pr-benzyl | H | |
| 20 | 3-O-i-Pr-benzyl | H | |
| 21 | 3-OCH$_2$F-benzyl | H | |
| 22 | 3-OCH$_2$Cl-benzyl | H | |
| 23 | 2-OCF$_3$-benzyl | H | |
| 24 | 4-OCF$_3$-benzyl | H | 142.1~144.5 |
| 25 | 4-OH-benzyl | H | 201.2~203.4 |

| Example | R¹ | R² | m.p. (°C.) |
|---|---|---|---|
| 26 | 4-ethoxyphenyl (H₅C₂O-C₆H₄-) | H | |
| 27 | 3,5-dimethyl-4-hydroxyphenyl (H₃C, HO, CH₃ substituted) | H | |
| 28 | 4-hydroxy-3-methoxyphenyl (HO, OCH₃) | H | |
| 29 | 3-hydroxyphenyl | H | |
| 30 | 3,4-dihydroxyphenyl (HO, OH) | H | |
| 31 | 3,5-di-t-butyl-4-hydroxyphenyl (t-Bu, HO, t-Bu) | H | |
| 32 | 3,5-dimethoxy-4-hydroxyphenyl (H₃CO, HO, OCH₃) | H | |
| 33 | 2-ethoxyphenyl (OC₂H₅) | H | 156.2–157.8 |
| 34 | 2,3-dihydroxyphenyl (OH, OH) | H | 220.1–221.7 |
| 35 | 3-amino-4-hydroxy-5-methylphenyl (H₂N, HO, CH₃) | H | |
| 36 | 3,4-dihydroxyphenyl (HO, OH) | H | |
| 37 | 2,6-dihydroxyphenyl (OH, OH) | H | |
| 38 | 3,5-dihydroxyphenyl (HO, OH) | H | |
| 39 | 3,4,5-trihydroxyphenyl (HO, HO, OH) | H | |
| 40 | 3-(tribromomethoxy)phenyl (OCBr₃) | H | 148.2–149.7 |

Example 41. 10-(2'-methylbenzyloxy)-Ginkgolide B

To a solution of 50 mg of Ginkgolide B in 5 ml of tetrahydrofuran was added 16 mg of potassium hydride followed by stirring, in an inert atmosphere, at room temperature for 5 minutes. To the mixture was then added 76 mg of 2-methylbenzyl bromide, followed by stirring at room temperature for 4 hours.

The mixture was treated with 0.5 ml of c-HCl at 0° C., diluted with 10 ml of water and extracted with 50 ml of ethylacetate. The solution was washed with 10 ml of water and dried over anhydrous magnesium sulfate. After filtering off, the filtrate was concentrated under reduced pressure. The residue was subjected to chromatography on silica gel (elution solvent: chloroform/methanol =99/1) to give 57 mg (91%) of the desired compound.

$^1$H-NMR (CDCl$_3$); δ 7.33–7.19(m, 4H), 5.99(5, 1H), 5.31(brs, 1H), 5.13 (ABq, J=9.3 Hz, Δυ=282 Hz), 4.91 (s, 1H), 4.52 (d, 1H, J=8.1 Hz), 4.23 (dd, 1H, J=8.1, 3.0 Hz), 3.05 (q, 1H, J=6.9 Hz), 2.90 (s, H), 2.75 (d, 1H, J=3.0 Hz), 2.41 (s, 3H), 2.27 (m, 1H), 1.98–1.90 (m, 2H), 1.29 (d, 3H, J=6.9 Hz), 1.14 (s, 9H).

Example 42.
1,10-bis(2'-methylbenzyloxy)-Ginkgolide B

To a solution of 50 mg of Ginkgolide B in 5 ml of tetrahydrofuran was added 16 mg of potassium hydride followed by stirring, in an inert atmosphere, at room temperature for 5 minutes. To the mixture was then added 152 mg of 2-methylbenzyl bromide, followed by stirring at room temperature for 4 hours.

The mixture was treated with 0.5 ml of c-HCl at 0° C., diluted with 10 ml of water and extracted with 50 ml of ethylacetate. The solution was washed with 10 ml of water and dried over anhydrous magnesium sulfate. After filtering off, the filtrate was concentrated under reduced pressure. The residue was subjected to chromatography on silica gel (elution solvent: chloroform/methanol =99/1) to give 34 mg (45%) of the desired compound.

$^1$H-NMR (CDCl$_3$); δ 7.22–6.84(m, 8H), 5.99(5, 1H), 5.69(d, 1H, J=3.6 Hz), 5.02(ABq, 2H, J=11.1 Hz, Δυ =177 Hz), 4.83 (s, 1H), 399 (d, 1H, J=12.0 Hz), 3.22 (q, 1H, J=6.9 Hz), 2.95 (s, 1H), 2.36–1.90 (m, 3H), 2.20 (s, 3H), 1.98 (s, 3H), 1.31 (d, 3H, J=6.9 Hz), 1.04 (s, 9H).

Example 43. 10-(4'-methylbenzyloxy)-Ginkgolide B

To a solution of 50 mg of Ginkgolide B in 5 ml of tetrahydrofuran was added 16 mg of potassium hydride followed by stirring, in an inert atmosphere, at room temperature for 5 minutes. To the mixture was then added 76 mg of 4-methylbenzyl bromide, followed by stirring at room temperature for 4 hours.

The mixture was treated with 0.5 ml of c-HCl at 0° C., diluted with 10 ml of water and extracted with 50 ml of ethylacetate. The solution was washed with 10 ml of water and dried over anhydrous magnesium sulfate. After filtering off, the filtrate was concentrated under reduced pressure. The residue was subjected to chromatography on silica gel (elution solvent: chloroform/methanol =99/1) to give 55 mg (87%) of the desired compound.

$^1$H-NMR (CDCl$_3$); δ 7.24–7.14 (m, 4H), 5.98 (s, 1H), 5.30 (brs, 1H), 5.02(ABq, J=9.0 Hz, Δυ=270 Hz), 4.89(s, 1H), 4.52 (d, 1H, J=8.1 Hz), 4.26 (dd, 1H, J=8.1, 3.0 Hz), 3.05 (q, 1H, J=6.9 Hz), 2.82 (brs, 2H), 2.36(s, 3H), 2.28(m, 1H), 1.93(brs, 2H), 1.29 (d, 3H, J=6.9 Hz), 1.14 (s, 9H).

Examples 44 to 77

In the same manner as in Example 43, the following compounds were prepared.

| Example | R$^1$ | R$^2$ | m.p. (°C.) |
|---|---|---|---|
| 44 | 4-O$_2$N-C$_6$H$_4$-CH$_2$- | H | |
| 45 | 2-C$_2$H$_5$-C$_6$H$_4$-CH$_2$- | H | |
| 46 | 4-C$_2$H$_5$-C$_6$H$_4$-CH$_2$- | H | |
| 47 | 4-i-Pr-C$_6$H$_4$-CH$_2$- | H | |
| 48 | 3-i-Pr-C$_6$H$_4$-CH$_2$- | H | |
| 49 | 3-n-Bu-C$_6$H$_4$-CH$_2$- | H | |
| 50 | 4-n-Bu-C$_6$H$_4$-CH$_2$- | H | 119.2~120.7 |
| 51 | 2-CF$_3$-C$_6$H$_4$-CH$_2$- | H | 162.1~164.5 |
| 52 | 2-CCl$_3$-C$_6$H$_4$-CH$_2$- | H | |
| 53 | 3-CCl$_3$-C$_6$H$_4$-CH$_2$- | H | |
| 54 | 4-CCl$_3$-C$_6$H$_4$-CH$_2$- | H | |
| 55 | 2-CBr$_3$-C$_6$H$_4$-CH$_2$- | H | |
| 56 | 3-CBr$_3$-C$_6$H$_4$-CH$_2$- | H | |
| 57 | 4-CBr$_3$-C$_6$H$_4$-CH$_2$- | H | |
| 58 | 2-CH$_2$F-C$_6$H$_4$-CH$_2$- | H | |
| 59 | 3-CH$_2$F-C$_6$H$_4$-CH$_2$- | H | 132.7~134.3 |
| 60 | 4-CH$_2$F-C$_6$H$_4$-CH$_2$- | H | 129.5~131.3 |

| Example | R¹ | R² | m.p. (°C.) |
|---|---|---|---|
| 61 | 2-(chloromethyl)phenyl-ethyl | H | |
| 62 | 3-(chloromethyl)phenyl-ethyl | H | |
| 63 | 3-nitrophenyl-ethyl | H | |
| 64 | 4-(bromomethyl)phenyl-ethyl | H | 137.2–138.6 |
| 65 | 4-phenoxyphenyl-ethyl | H | 157–159 |
| 66 | 3-benzylphenyl-ethyl | H | |
| 67 | 1-phenylpropyl (H₃C-CH(Ph)-CH₂-) | H | |
| 68 | 4-(2-phenylethyl)phenyl-ethyl | H | |
| 69 | 2'-bromobiphenyl-4-yl-ethyl | H | |
| 70 | 2',3'-dichlorobiphenyl-4-yl-ethyl | H | |
| 71 | 3'-ethylbiphenyl-4-yl-ethyl (C₂H₅) | H | |
| 72 | 2'-methoxybiphenyl-4-yl-ethyl (OCH₃) | H | |
| 73 | 3,4-dihydroxybiphenyl-4'-yl-ethyl | H | 175–177 |
| 74 | 3-aminophenyl-ethyl (NH₂) | H | 119–123 |
| 75 | 4-aminophenyl-ethyl (H₂N) | H | |
| 76 | 3-(dimethylamino)phenyl-ethyl (N(CH₃)₂) | H | |
| 77 | 4-(dimethylamino)phenyl-ethyl ((CH₃)₂N) | H | 185.2–186.7 |

Example 78. 10-(3'-phenoxypropoxy)-Ginkgolide B

To a solution of 50 mg of Ginkgolide B in 5 ml of tetrahydrofuran was added 16 mg of potassium hydride followed by stirring, in an inert atmosphere, at room temperature for 5 minutes. To the mixture was then added 117 mg of 3-phenoxypropyltrifluoromethanesulfonate, followed by stirring at room temperature for 4 hours.

The mixture was treated with 0.5 ml of c-HCl at 0° C., diluted with 10 ml of water and extracted with 50 ml of ethylacetate. The solution was washed with 10 ml of water and dried over anhydrous magnesium sulfate. After filtering off, the filtrate was concentrated under reduced pressure. The residue was subjected to chromatography on silica gel (elution solvent: chloroform/methanol =99/1) to give 63 mg (95%) of the desired compound.

$^1$H-NMR (CDCl$_3$); δ 7.31(t, 2H, J=7.8 Hz), 7.02(t, 1H, J=7.8 Hz), 6.92 (d, 2H, J=7.8 Hz), 5.95 (s, 1H), 5.59 (m, 1H), 5.43 (brs, 1H), 4.78 (m, 1H), 4.70 (s, 1H), 4.66 (d, 1H, J=8.1 Hz), 4.35 (dd, 1H, J=8.1, 3.0 Hz), 4.10–3.82 (m, 4H), 3.86 (d, 1H, J=3.0 Hz), 3.06 (q, 1H, J=6.9 Hz), 2.97 (s, 1H), 2.2S-1.80(m, 3H), 1.31(d, 3H, J=6.9 Hz), 1.03 (s, 9H).

Example 79. 10-(2'-phenylethoxy)-Ginkgolide B

To a solution of 50 mg of Ginkgolide B in 5 ml of tetrahydrofuran was added 16 mg of potassium hydride followed by stirring, in an inert atmosphere, at room temperature for 5 minutes. To the mixture was then added 83 mg of 2-phenycthyl-methanesulfonate, followed by stirring at 70° C. for 4 hours.

The mixture was treated with 0.5 ml of c-HCl at 0° C., diluted with 10 ml of water and extracted with 50 ml of ethylacetate. The solution was washed with 10 ml of water and dried over anhydrous magnesium sulfate. After filtering off, the filtrate was concentrated under reduced pressure. The residue was subjected to chromatography on silica gel (elution solvent: chloroform/methanol =99/1) to give 46 mg (73%) of the desired compound.

$^1$H-NMR (CDCl$_3$); δ 7.30(m, 5H), 5.90(s, 1H), 5.27(d, 1H, J=3.9 Hz), 4.89 (m, 1H), 4.64 (s, 1H), 4.54 (d, 1H, J=7.8 Hz), 4.16 (dd, 1H, J=7.8, 3.0 Hz), 3.80 (m, 1H), 2.98 (m, 3H), 2.13 (dd, 1H, J=13.6, 3 Hz), 1.84 (dd, 1H, J=13.6, 3 Hz), 1.79 (m, 1H), 1.27 (d, 3H, J=6 Hz), 1.05 (s, 9H).

Example 80.
10-(3',4'.5'-trimethoxybenzoyloxy)-Ginkgolide B

To a solution of 50 mg of Ginkgolide B in 5 ml of pyridine was added 1 mg of N,N-dimethylaminopyridine and 95 mg of 3,4,5-trimethoxybenzoyl chloride, in an inert atmosphere, at room temperature. The mixture was stirred at room temperature for 4 hours.

The mixture was treated with 50 ml of 2N HCl at 0° C., diluted with 10 ml of water and extracted with 150 ml of ethylacetate. The solution was washed with 20 ml of water and dried over anhydrous magnesium sulfate. After filtering off, the filtrate was concentrated under reduced pressure. The residue was subjected to chromatography on silica gel (elution solvent: chloroform/methanol=99/1) to give 50 mg (68%) of the desired compound.

$^1$H-NMR (CDCl$_3$); δ 7.33 (5, 2H), 6.21 (s, 1H), 6.15 (s, 1H), 5.60(d, 1H, J=7.7 Hz), 5.29(s, 1H), 4.65(d, 1H, J=7.2 Hz), 4.40(d, 1H, J=6.9 Hz), 4.12(q, 1H, J=3.0 Hz), 3.90 (d, 9H, J=9.0 Hz), 3.10 (q, 1H, J=6.9 Hz), 2.37 (m, 1H), 2.04 (m, 2H), 1.28 (d, 3H, J=6.9 Hz), 1.04 (s, 9H).

Example 81. 10-(4'-phenylbenzyloxy)-Ginkgolide B

To a solution of 50 mg of Ginkgolide B in 5 ml of tetrahydrofuran was added 16 mg of potassium hydride followed by stirring, in an inert atmosphere, at room temperature for 5 minutes. To the mixture was then added 121 mg of 4-phenylbenzyl iodide, followed by stirring at room temperature for 4 hours.

The mixture was treated with 0.5 ml of c-HCl at 0° C., diluted with 10 ml of water and extracted with 50 ml of ethylacetate. The solution was washed with 10 ml of water and dried over anhydrous magnesium sulfate. After filtering off, the filtrate was concentrated under reduced pressure. The residue was subjected to chromatography on silica gel (elution solvent: chloroform/methanol =99/1) to give 57 mg (82%) of the desired compound.

$^1$H-NMR (CDCl$_3$); δ 7.63 (m, 4H), 7.42 (m, 5H), 6.00 (s, 1H), 5.34(brs, 1H), 5.09(ABq, 2H, J=9.3, Δυ=270 Hz), 4.94 (5, 1H), 4.55 (d, 1H, J=7.8 Hz), 4.31 (dd, 1H, J=7.8, 2.7 Hz), 3.06 (q, 1H, J=6.9 Hz), 2.98 (s, 1H), 2.89 (d, 1H, J=7.8, 2.7 Hz), 2.29 (m, 1H), 1.95 (brs, 2H), 1.30 (d, 3H, J=6.9 Hz), 1.16 (s, 9H).

Example 82. 10-piperonyloxy-Ginkgolide B

To a solution of 50 mg of Ginkgolide B in 5 ml of tetrahydrofuran was added 16 mg of potassium hydride followed by stirring, in an inert atmosphere, at room temperature for minutes. To the mixture was then added 108 mg of piperonyl iodide, followed by stirring at room temperature for 4 hours. The mixture was treated with 0.5 ml of c-HCl at 0° C., diluted with 10 ml of water and extracted with 50 ml of ethylacetate. The solution was washed with 10 ml of water and dried over anhydrous magnesium sulfate. After filtering off, the filtrate was concentrated under reduced pressure. The residue was subjected to chromatography on silica gel (elution solvent: chloroform/methanol =99/1) to give 59 mg (89%) of the desired compound.

$^1$H-NMR (CDCl$_3$);δ 6.84(d, 1H, J=3.0Hz), 6.83(d, 1H, J=9.0 Hz), 6.82(dd, 1H, J=9.0, 3.0 Hz), 5.99(5, 2H), 5.98 (s, 1H), 5.31 (brs, 1H), 4.94 (ABq, 2H, J=9.0 Hz, Δυ=258 Hz), 4.87 (s, 1H), 4.51 (d, 1H, J=9.0 Hz), 4.24 (d, 1H, J=9.0, 3.0 Hz), 3.22 (s, 1H), 3.04 (q, 1H, J=6.0 Hz), 2.88 (d, 1H, J=3.0 Hz), 2.28 (brd, 1H, J=6.0 Hz), 1.93 (s, 2H), 1.29 (d, 3H, J=6.0 Hz), 1.13 (s, 9H).

Example 83.
10-(2',3',4',5',6'-pentafluorobenzyloxy)-Ginkgolide B

To a solution of 50 mg of Ginkgolide B in 5 ml of tetrahydrofuran was added 16 mg of potassium hydride followed by stirring, in an inert atmosphere, at room temperature for 5 minutes. To the mixture was then added 108 mg of α-bromo-2,3,4,5,6-pentafluorotoluene, followed by stirring at room temperature for 4 hours.

The mixture was treated with 0.5 ml of c-HCl at 0° C., diluted with 10 ml of water and extracted with 50 ml of ethylacetate. The solution was washed with 10 ml of water and dried over anhydrous magnesium sulfate. After filtering off, the filtrate was concentrated under reduced pressure. The residue was subjected to chromatography on silica gel (elution solvent: chloroform/methanol=99/1) to give 53 mg (74%) of the desired compound.

$^1$H-NMR (CDCl$_3$); δ 6.00(s, 1H), 5.36(brs, 1H), 5.22(ABq, 2H, J=10.8 Hz, Δυ=243 Hz), 4.92(s, 1H), 4.58(d, 1H, J=6.0 Hz), 4.27(dd, 1H, J=6.0, 3.0 Hz), 3.04(s, 1H), 3.02(brs, 1H), 2.78(brs, 1H), 2.27 (d, 1H, J=9.0, 3.0 Hz), 1.90 (m, 2H), 1.29 (d, 3H, J=6.0 Hz), 1.10 (s, 9H).

Example 84. 10-(3'-fluorobenzyloxy)-Ginkgolide B

To a solution of 50 mg of Ginkgolide B in 5 ml of tetrahydrofuran was added 16 mg of potassium hydride followed by stirring, in an inert atmosphere, at room temperature for 5 minutes. To the mixture was then added 78 mg of 3-fluorobenzyl bromide, followed by stirring at room temperature for 4 hours.

The mixture was treated with 0.5 ml of c-HCl at 0° C., diluted with 10 ml of water and extracted with 50 ml of ethylacetate. The solution was washed with 10 ml of water and dried over anhydrous magnesium sulfate. After filtering off, the filtrate was concentrated under reduced pressure. The residue was subjected to chromatography on silica gel (elution solvent: chloroform/methanol =99/1) to give 52 mg (83%) of the desired compound.

$^1$H-NMR (CDCl$_3$); δ 7.40(m, 1H), 7.10(m, 3H), 5.99(5, 1H), 5.34 (5, 1H), 5.04 (ABq, 2H, J=9.3 Hz, Δυ=263 Hz), 4.91 (s, 1H), 4.54 (d, 1H, J=7.8 Hz), 4.26 (d, 1H, J=7.8 Hz), 3.05 (m, 2H), 2.78 (s, 1H), 2.30(d, 1H, J=7.5 Hz), 1.94(s, 2H), 1.29 (d, 3H, J=6.6 Hz), 1.14 (s, 9H).

Example 85. 10-(4'-fluorobenzyloxy)-Ginkgolide B

To a solution of 50 mg of Ginkgolide B in 5 ml of tetrahydrofuran was added 16 mg of potassium hydride followed by stirring, in an inert atmosphere, at room temperature for 5 minutes. To the mixture was then added 78 mg of 4-fluorobenzyl bromide, followed by stirring at room temperature for 4 hours.

The mixture was treated with 0.5 ml of c-HCl at 0° C., diluted with 10 ml of water and extracted with 50 ml of ethylacetate. The solution was washed with 10 ml of water and dried over anhydrous magnesium sulfate. After filtering off, the filtrate was concentrated under reduced pressure. The residue was subjected to chromatography on silica gel (elution solvent: chloroform/methanol =99/1) to give 53 mg (85%) of the desired compound.

$^1$H-NMR (CDCl$_3$);δ 7.35(m, 2H), 7.10(m, 2H), 5.98(s, 1H), 5.30(brs, 1H), 5.01(ABq, 2H, J=9.6 Hz, Δυ=267 Hz), 4.90 (s, 1H), 4.53 (d, 1H, J=7.8 Hz), 4.25(d, 1H, J=7.8 Hz), 3.04(q, 1H, J=6.9 Hz), 2.27 (d, 1H, J=9.3 Hz), 2.08 (m, 1H), 1.93 (m, 1H), 1.26 (d, 3H, J=6.9 Hz), 1.16 (s, 9H).

Example 86.
10-(2',4'-difluorobenzyloxy)-Ginkgolide B

To a solution of 50 mg of Ginkgolide B in 5 ml of tetrahydrofuran was added 16 mg of potassium hydride followed by stirring, in an inert atmosphere, at room temperature for minutes. To the mixture was then added 105 mg of 2,4-difluorobenzyl iodide, followed by stirring at room temperature for 4 hours.

The mixture was treated with 0.5 ml of c-HCl at 0° C., diluted with 10 ml of water and extracted with 50 ml of ethylacetate. The solution was washed with 10 ml of water and dried over anhydrous magnesium sulfate. After filtering off, the filtrate was concentrated under reduced pressure. The residue was subjected to chromatography on silica gel (elution solvent: chloroform/methanol =99/1) to give 45 mg (85%) of the desired compound.

$^1$H-NMR (CDCl$_3$);δ 7.40 (q, 1H, J=6.0 Hz), 6.92 (m, 2H), 5.32 (d, 1H, J=3.0 Hz), 5.10 (ABq, 2H, J=9.9 Hz, Δυ=196 Hz), 4.91 (s, 1H), 4.54 (d, 1H, J=7.8 Hz), 4.24 (dd, 1H, J=7.8, 3.0 Hz), 3.04 (q, 1H, J=6.0 Hz), 2.81 (d, 1H, J=3.0 Hz), 2.26 (m, 1H), 1.90 (m, 2H), 1.29 (d, 3H, J=6.0 Hz), 1.12 (s, 9H).

Example 87. 10-(2'-fluorobenzyloxy)-Ginkgolide B

To a solution of 50 mg of Ginkgolide B in 5 ml of tetrahydrofuran was 16 mg of potassium hydride followed by stirring, in an inert atmosphere, at room temperature for 5 minutes. To the mixture was then added 78 mg of 2-fluorobenzyl bromide, followed by stirring at room temperature for 4 hours.

The mixture was treated with 0.5 ml of c-HCl at 0° C., diluted with 10 ml water and extracted with 50 ml of ethylacetate. The solution was washed with 10 ml of water and dried over anhydrous magnesium sulfate. After filtering off, the filtrate was concentrated under reduced pressure. The residue was subjected to chromatography on silica gel (elution solvent: chloroform/methanol =99/1) to give 49 mg (79%) of the desired compound.

$^1$H-NMR (CDCl$_3$); δ 7.40 (brs, 2H), 7.19 (m, 2H), 5.98 (s, 1H), 5.31 (s, 1H), 5.14 (ABq, 2H, J=9.6 Hz, Δυ=196 Hz), 4.92 (s, 1H), 4.54 (d, 1H, J=7.8 Hz, 4.26(brs, 1H), 3.05(m, 2H), 2.86(s, 1H), 2.25 (m, 1H), 1.9 1 (s, 2H), 1.29 (d, 3H, J=6.4 Hz), 1.10 (s, 9H).

Example 88. 10-benzoyloxy-Ginkgolide B

To a solution of 50 mg of Ginkgolide B in 5 ml of pyridine was added 1 mg of N,N-dimethylaminopyridine and 100 mg of benzoyl chloride, in an inert atmosphere, at room temperature. The mixture was stirred at room temperature for 4 hours.

The mixture was then treated with 50 ml of 2N-HCl at 0° C., diluted with 20 ml of water and extracted with 150 ml of ethylacetate. The solution was washed with 10 ml of water and dried over anhydrous magnesium sulfate. After filtering off, the filtrate was concentrated under reduced pressure. The residue was subjected to chromatography on silica gel (elution solvent: chloroform/methanol=99/1) to give 22 mg (35%) of the desired compound.

$^1$H-NMR (CDCl$_3$); δ 8.05 (d, 2H, J=7.8 Hz), 7.63 (t, 1H, J=7. 5Hz), 7.50(t, 2H, J=7.5Hz), 6.27(s, 1H), 6.15 (s, 1H), 5.64 (d, 1H, J=3.6 Hz), 4.65 (d, 1H, J=7.2 Hz), 4.31(brs, 1H), 3.10(q, 1H, J=6.9 Hz), 2.38 (d, 1H, J=9.0 Hz), 2.02 (d, 2H, J=5.7 Hz), 1.28(d, 3H, J=6.9 Hz), 1.05(s, 9H).

Example 89. 1-benzoyloxy-Ginkgolide B

In the same manner as in Example 88, the title compound was prepared (18 mg 29%).

$^1$H-NMR (CDCl$_3$); δ 7.93(d, 2H, J=7.5Hz), 7.62(t, 1H, J=7.5Hz), 7.93(t, 2H, J=7.5Hz), 6.02(s, 1H), 5.78(d, 1H, J=6.9 Hz), 5.65 (d, 1H, J=3.6 Hz), 5.04 (s, 1H), 4.76 (d, 1H, J=6.9 Hz), 3.21 (q, 1H, J=7.2 Hz), 2.38 (dd, 1H, J=7.2, 3.0 Hz), 2.00 (m, 2H), 1.32 (d, 3H, J=7.2 Hz), 1.09 (s, 9H).

Example 90. 10-benzenesulfonyloxy-Ginkgolide B

To a solution of 50 mg of Ginkgolide B in 5 ml of pyridine was added 150 mg of benzenesulfonyl chloride followed by stirring, in an inert atmosphere, at room temperature. After 4 hours stirring at room temperature.

The mixture was treated with 30 ml of 2N-HCL at 0° C., diluted with 20 ml of water and extracted with 150 ml of ethylacetate. The solution was washed with 10 ml of water and dried over anhydrous magnesium sulfate. After filtering off, the filtrate was concentrated under reduced pressure. The residue was subjected to chromatography on silica gel (elution solvent: chloroform/methanol=99/1) to give 41 mg (62%) of the desired compound.

$^1$H-NMR (CDCl$_3$); δ 8.02(d, 2H, J=6.0 Hz), 7.76(t, 1H, J=6.0 Hz), 7.63 (t, 2H, J=6.0 Hz), 6.05 (s, 1H), 5.96(s, 1H), 5.45(d, 1H, J=3.0 Hz), 4.56(d, 1H, J=7.5 Hz), 4.04 (dd, 1H, J=7.5 Hz, 3.0 Hz), 3.06 (s, 1H), 2.91 (q, 1H, J=6.0 Hz), 2.75 (s 1H), 2.29 (d, 1H, J=9.0 Hz), 1.97 (s, 2H), 1.25 (d, 3H, J=6.0 Hz), 1.15 (s, 9H).

Example 91. 10-(3'-methoxybenzyloxy)-Ginkgolide B

To a solution of 50 mg of Ginkgolide B in 5 ml of tetrahydrofuran was added 16 mg of potassium hydride followed by stirring, in an inert atmosphere, at room temperature for 5 minutes. To the mixture was then added 102 mg of 3-methoxybenzyl bromide, followed by stirring at room temperature for 4 hours.

The mixture was treated with 0.5 ml of c-HCl at 0° C., diluted with 10 ml of water and extracted with 50 ml of ethylacetate. The solution was washed with 10 ml of water and dried over anhydrous magnesium sulfate. After filtering off, the filtrate was concentrated under reduced pressure. The residue was subjected to chromatography on silica gel (elution solvent: chloroform/methanol =99/1) to give 48 mg (75%) of the desired compound.

$^1$H-NMR (CDCl$_3$); δ 7.33 (t, 1H, J=7.8 Hz), 6.93 (d, 2H, J=7.8 Hz), 6.87(s, 1H), 5.99(5, 1H), 5.32(brs, 1H), 5.04 (ABq, 2H, J=9.3 Hz, Δυ=267 Hz), 4.90(s, 1H), 4.54(d, 1H, J=7.8 Hz), 4.28(brd, 1H), 3.82(s, 3H), 3.05(q, 1H, J=6.9 Hz), 2.87 (brs, 2H), 2.29 (m, 1H), 1.94 (m, 2H), 1.30 (d, 3H, J=6.9 Hz), 1.14 (s, 9H).

Example 92.
1,10-bis(2',4'-dichlorobenzyloxy)-Ginkgolide B

To a solution of 50 mg of Ginkgolide B in 5 ml of tetrahydrofuran was added 16 mg of potassium hydride followed by stirring, in an inert atmosphere, at room temperature for 5 minutes. To the mixture was then added 260 mg of 2,4-dichlorobenzyliodide, followed by stirring at room temperature for 4 hours.

The mixture was treated with 0.5 ml of c-HCl at 0° C., diluted with 10 ml of water and extracted with 50 ml of ethylacetate. The solution was washed with 10 ml of water and dried over anhydrous magnesium sulfate. After filtering off, the filtrate was concentrated under reduced pressure. The residue was subjected to chromatography on silica gel (elution solvent: chloroform/methanol =99/1) to give 40 mg (45%) of the desired compound.

$^1$H-NMR (CDCl$_3$); δ 7.21–6.88(m, 6H), 6.02(s, 1H), 5.64(d, 1H, J=3.6 Hz), 5.02 (ABq, 2H, J=10.5, Δυ=207 Hz), 4.85(s, 1H), 4.59(d, 1H, J=13.5 Hz), 4.43(ABq, 2H, J=6.3 Hz, Δυ=168 Hz), 3.94 (d, 1H, J=13.5 Hz), 3.30 (q, 1H, J=6.9 Hz), 2.93 (s, 1H), 2.40–1.90(m, 3H), 1.32(d, 3H, J=6.9 Hz), 1.13 (s, 9H).

Example 93.
10-(3'-trifluoromethylbenzyloxy)-Ginkgolide B

To a solution of 50 mg of Ginkgolide B in 5 ml of tetrahydrofuran was added 16 mg of potassium hydride followed by stirring, in an inert atmosphere, at room temperature for 5 minutes. To the mixture was then added 99 mg of 4-trifluoromethylbenzyl bromide, followed by stirring at room temperature for 4 hours.

The mixture was treated with 0.5 ml of c-HCl at 0° C., diluted with 10 ml of water and extracted with 50 ml of ethylacetate. The solution was washed with 10 ml of water and dried over anhydrous magnesium sulfate. After filtering off, the filtrate was concentrated under reduced pressure. The residue was subjected to chromatography on silica gel (elution solvent: chloroform/methanol =991 1) to give 45 mg (65%) of the desired compound.

$^1$H-NMR (CDCl$_3$); δ 7.67–7.58(m, 4H), 6.00(s, 1H), 5.34(brs, 1H), 5.12 (ABq, 2H, J=9.9, Δυ=267 Hz), 4.93 (5, 1H), 4.55 (d, 1H, J=7.8 Hz), 4.26 (dd, 1H, J=7.8, 2.4 Hz), 3.05(q, 1H, J=6.9 Hz), 2.86(s, 1H), 2.68 (d, 1H, J=2.4 Hz), 2.31 (m, 1H), 1.94 1.90(m, 2H), 1.30(d, 3H, J=6.9 Hz), 1.14(s, 9H).

Example 94.
10-(4'-trifluoromethylbenzyloxy)-Ginkgolide B

To a solution of 50 mg of Ginkgolide B in 5 ml of tetrahydrofuran was added 16 mg of potassium hydride followed by stirring, in an inert atmosphere, at room temperature for 5 minutes. To the mixture was then added 99 mg of 4-trifluoromethylbenzyl bromide, followed by stirring at room temperature for 4 hours.

The mixture was treated with 0.5 ml of c-HCl at 0° C., diluted with 10 ml of water and extracted with 50 ml of ethylacetate. The solution was washed with 10 ml of water and dried over anhydrous magnesium sulfate. After filtering off, the filtrate was concentrated under reduced pressure. The residue was subjected to chromatography on silica gel (elution solvent: chloroform/methanol =99/1) to give 39 mg (58%) of the desired compound.

$^1$H-NMR (CDCl$_3$); δ 7.70(d, 2H, J=7.8 Hz), 7.49(d, 2H, J=7.8 Hz), 6.01(s, 1H), 5.33(brs, 1H), 5.12(ABq, 2H, J=10.2, Δυ=279 Hz), 4.92(s, 1H), 4.54(d, 1H, J=7.8 Hz), 4.28 (dd, 1H, J=7.8, 3.0 Hz), 3.05 (q, 1H, J=6.9 Hz), 2.86 (s, 1H), 2.69 (d, 1H, J=3.0 Hz), 2.3 ! (m, 1H), 1.95–1.91 (m, 2H), 1.27 (d, 3H, J=6.9 Hz), 1.15 (s, 9H).

Example 95. 1,10-bis 4'-trifluoromethylbenzyloxy)-Ginkgolide B

To a solution of 50 mg of Ginkgolide B in 5 ml of tetrahydrofuran was added 16 mg of potassium hydride followed by stirring, in an inert atmosphere, at room temperature for minutes. To the mixture was then added 198 mg of 4-trifluoromethylbenzylbromide, followed by stirring at room temperature for 4 hours.

The mixture was treated with 0.5 ml of c-HCl at 0° C., diluted with 10 ml of water and extracted with 50 ml of ethylacetate. The solution was washed with 10 ml of water and dried over anhydrous magnesium sulfate. After filtering off, the filtrate was concentrated under reduced pressure. The residue was subjected to chromatography on silica gel (elution solvent: chloroform/methanol =99/1) to give 33 mg (38%) of the desired compound.

$^1$H-NMR (CDCl$_3$); δ 7.41(d, 2H, J=8.1 Hz), 7.24(s, 4H), 6.88 s, H), 6.03 (s, 1H), 5.63 (d, 1H, J=3.6 Hz), 5.07 ABq, 2H, J=11.4, Δυ=270 Hz), 4.88 (s), 1H), 4.64 (d, 1H, J=12.0 Hz), 4.45 (ABq, 2H, J=6.6, Δυ=162 Hz), 4.15 (d, 1H, J=12.0 Hz), 3.21 (q, 1H, J=7.2 Hz), 2.95 (s, 1H), 2.37 (dd, 1H, J=13.2, 3.9 Hz), 2.11 (td, 1H, J=8.2, 3.9 Hz), 1.97(dd, 1H, J=14.4, 3.9 Hz), 1.33 (d, 3H, J=7.2 Hz), 1.13 (s, 9H).

Example 96. 10- (3,5-dimethyl-2-pyridinyl)-methoxy-Ginkgolide

To a solution of 2.0 g of Ginkgolide B in 50 ml of tetrahydrofuran was added 1.5 g of 35% potassium hydride followed by stirring, in an inert atmosphere, at room temperature for 5 minutes. To the mixture was then added 2.2 g of 3,5-dimethyl-2-picolyl bromide and refluxed under heating with stirring for 1 hours.

The mixture was treated with 4 ml of 6N HCl at 0° C., diluted with 10 ml of water and extracted with 50 ml of ethylacetate. The solution was washed with 10 ml of water and dried over anhydrous magnesium sulfate. After filtering off, the filtrate was concentrated under reduced pressure. The residue was subjected to chromatography on silica gel (elution solvent: chloroform/methanol =99/1) to give 1.97 g (77%) of the desired compound.

¹H-NMR (CDCl₃); δ 8.20(brs, 1H), 7.33(brs, 1H), 5.99(5, 1H), 5.63 (brd, 1H), 5.14 (ABq, 2H, JAB =15 Hz, Δυ=228 Hz), 4.97 (5, 1H), 4.64 (d, 1H, J =7.5 Hz), 4.44(d, 1H, J =7.5 Hz), 3.07(q, 1H, J=6.9 Hz), 2.86(brs, 1H), 2.30(s, 3H), 2.17(s, 3H), 2.25–1.93 (overlapping m, 3H), 1.30 (d, 3H, J =6.9 Hz), 1.11 (2, 9H).

Example 97. 10- (4-methoxy-3,5-dimethyl-2-pyridinyl) -methoxy-Ginkgolide B

To a solution of 100 mg of Ginkgolide B in 8 ml of tetrahydrofuran was added 137 mg of 35% potassium hydride followed by stirring, in an inert atmosphere, at room temperature for 3 minutes. To the mixture was then added 65 mg of 4-methoxy-3,5-dimethyl-2-picolyl chloride and refluxed under heating with stirring for 10 hours.

The mixture was treated with 0.5 ml of 6N HCl at 0° C., diluted with 10 ml of water and extracted with 50 ml of ethylacetate. The solution was washed with 10 ml of water and dried over anhydrous magnesium sulfate. After filtering off, the filtrate was concentrated under reduced pressure. The residue was subjected to chromatography on silica gel (elution solvent: chloroform/methanol=991 1) to give 76 mg (55%) of the desired compound.

¹H-NMR (CDCl₃); δ 8.15(s, 1H), 8.07(d, 1H, J=4.2 Hz), 6.40(s, 1H), 6.20 (s, 5.41 (brs, 2H), 5.09 (ABq, 2H, JAB= 14.4 Hz, Δυ=146 Hz), 4.63 (d, 1H, J=7.5 Hz), 4.16 (d, 1H, J=4.2 Hz), 3.75 (5, 3H), 2.91 (q, 1H J=7.2 Hz), 2.20 (s, 3H), 2.07 (s, 3H), 2.14–1.80 (m, 3H), 1.13 (d, 3H, J=7.2 Hz), 1.06 (s, 9H).

Example 98. 10-(3,5-dimethyl-4-nitro-2-pyridinyl)-methoxy-Ginkgolide B

To a solution of 2.5 g of Ginkgolide B in 50 ml of tetrahydrofuran was added 1.5 g of 35% potassium hydride followed by stirring, in an inert atmosphere, at room temperature for 5 minutes. To the mixture was then added 2.0 g of 3,5-dimethyl-4-nitro-2-picolyl chloride and refluxed under heating with stirring for 1 hour.

The mixture was treated with 4 ml of 6N HCl at 0° C., diluted with 20 ml of saturated sodium bicarbonate solution and extracted with 100 ml of dichloromethane. The solution was washed with 10 ml of water and dried over anhydrous magnesium sulfate. After filtering off, the filtrate was concentrated under reduced pressure. The residue was subjected to chromatography on silica gel (elution solvent: chloroform/methanol=99/1) to give 2.9 g (84%) of the desired compound.

¹H-NMR (CDCl₃); δ 8.44 (s, 1H), 7.65 (d, 1H, J=4.5 Hz), 6.00 (s, 1H), 5.60 (s, 1H), 5.22 (ABq, 2H, JAB=13.8 Hz, Δυ=231 Hz), 4.99 (5, 1H), 4.63 (d, 1H, J=7.5 Hz), 4.40 (dd, 1H, J=7.8 Hz, 4.5 Hz), 3.05 (q, 1H, J=6.9 Hz), 2.89 (s, 1H), 2.31 (s, 3H), 2.14 (s, 3H), 2.27–1.98 (overlapping m, 3H), 1.30 (d, 3H, J=6.9 Hz), 1.11 (s, 9H).

Example 99. 10-(2-pyridinyl)-methoxy-Ginkgolide B

In the same manner as in Example 97, the title compound was prepared using 160 mg of Ginkgolide B and 200 mg of 2-picolylchloride (78 mg, 40%).

Example 100. 10-(5-butyl-2-pyridinyl)-methoxy-Ginkgolide B

In the same manner as in Example 98, the title compound was prepared using 120 mg of Ginkgolide B and 200 mg of 5-butyl-2-picolyl chloride (118 mg, 74%)

¹H-NMR (DMSO-d₆); δ 8.37 (s, 1H), 7.54 (d, 1H, J=7.8 Hz), 7.04 (d, 1H, J=7.8 Hz), 5.98 (s, 1H), 5.60 (brs, 1H), 5.20 (ABq, 2H, JAB=12.6 Hz, Δυ=262 Hz), 4.92 (s, 1H), 4.64 (d, 1H, J=7.5 Hz), 4.46(d, 1H, J=7.5 Hz), 3.07(q, 1H, J=6.9 Hz), 2.62 (t, 2H, J=7.8 Hz), 2.27–1.96 (overlapping m, 3H), 1.60 (m, 2H), 1.38 (m, 2H), 1.30 (d, 3H, J=6.9 Hz), 1.10 (s, 9H), 0.93 (t, 3H, J=7.5 Hz).

Example 101. 10-(2-pyridinyl)-ethoxy-Ginkgolide B

To a solution of 120 mg of Ginkgolide B in 10 ml of tetrahydrofuran was added 137 mg of 35% potassium hydride followed by stirring, in an inert atmosphere, at room temperature for 5 minutes. To the mixture was then added 239 mg of 2-(2-trifluoromethanesulfonyloxyethyl)-pyridine and refluxed under heating with stirring for 1 hour.

The mixture was treated with 0.5 ml of 6N HCl at 0° C., diluted with 10 ml of water and extracted with 50 ml of dichloromethane. The solution was washed with 10 ml of water and dried over anhydrous magnesium sulfate. After filtering off, the filtrate was concentrated under reduced pressure. The residue was subjected to chromatography on silica gel (elution solvent: chloroform/methanol=99/1) to give 117 mg (78%) of the desired compound.

¹H-NMR (CDCl₃); δ 8.49(brd, 1H), 7.71(td, 1H, J=7.5 Hz, 1.5 Hz), 7.27–7.18(m, 2H), 5.89(s, 1H), 5.58 (brs, 1H), 4.66 (d, 1H, J=7.5 Hz), 4.63(s, 1H), 4.57(m, 1H), 4.26(d, 1H, J=7.5 Hz), 3.92 (m, 1H), 3.09–2.99 (overlapping m, 3H), 2.91(s, 1H), 2.23–1.89(overlapping m, 3H), 1.27 (d, 3H, J=6.9 Hz), 1.04 (s, 9H).

Example 102. 10-(2-quinolinyl)-methoxy-Ginkgolide B

In the same manner as in Example 101, the title compound was prepared using 55 mg of Ginkgolide B and 70 mg of 2-(iodomethyl)-quinoline (41 mg, 55%).

¹H-NMR (CDCl₃); δ 8.43(d, 1H, J=8.7 Hz), 8.05–8.00 (m, 2H), 7.95 (d, 1H, J=4.8 Hz), 7.83(t, 1H, J=7.8 Hz), 7.47 (t, 1H, J=7.8 Hz), 7.49(d, 1H, J=8.7 Hz), 6.47 (brs, 1H), 6.22 (s, 1H), 5.48(brd, 1H), 5.44 (5, 1H), 5.35 (ABq, 2H, J=15.0 Hz, Δυ=146 Hz), 4.74(d,1H, J=7.5 Hz), 4.32 (dd, 1H, J=7.5 Hz, 4.8 Hz), 2.89 (q, 1H, J=6.9 Hz), 2.30–1.70 (overlapping m, 3H), 1.13 (d, 3H, J=6.9 Hz), 1.07 (s, 9H).

Example 103. 10-(3,5-dimethyl-4-amino-2-pyridinyl)-methoxy-Ginkgolide B

To a mixture of 300 mg of 10-(3,5-dimethyl-4-nitro-2-pyridinyl)-methoxy Ginkgolide B obtained in Example 98, 1 ml of c-HCl, 8 ml of tefrahydrofuran and 4 ml of water, was added 233 mg of Zn with stirring at room temperature.

The mixture was stirred at room temperature for 1 hour and then, after filtering off, the filtrate was neutralized with 5 ml of saturated sodiumcarbonate solution and extracted with 50 ml of ethylacetate.

The solution was dried over anhydrous magnesium sulfate, filtered and concentrated. The residue was crystallized from ethyl ether to give 199 mg (70%) of the desired compound.

¹H-NMR (CD₃OD); δ 7.79(5, 1H), 6.1 1(s, 1H), 5.47(brs, 1H), 5.29 (s, 1H), 5.10 (ABq, 2H, JAB=20.3 Hz, Δυ=176 Hz), 4.55 (d, 1H, J=7.5 Hz), 4.36 (d, 1H, J=7.5 Hz), 3.05 (q, 1H, J=7.2 Hz), 2.11 (s, 3H), 1.99 (s, 3H), 2.15–1.98 (overlapping m, 3H), 1.24 (d, 3H, J=7.2 Hz), 1.21 (s, 1H).

Example 104.
10-(3,5-dimethyl-4-hydroxyamino-2-pyridinyl)-methoxy-Ginkgolide B To a mixture of 150 mg of 10-(3,5-dimethyl-4-nitro-2-pyridinyl)-methoxy Ginkgolide B obtained in Example 98 in 3 ml of tetrahydrofuran and 3 ml of water, was added 106 mg of Zn and 22 mg of $NH_4Cl$ followed by stirring at room temperature. The mixture was stirred at room temperature for 1 hour. After filtering off, the filtrate was extracted with 10 ml of ethylacetate. The solution was dried over anhydrous magnesium sulfate, filtered and concentrated. The residue was crystallized from ethyl ether to give 103 mg (70%) of the desired compound.

$^1$H-NMR ($CD_3OD$); δ 7.93(5, 1H), 6.12(s, 1H), 5.49(5, 1H), 5.31 (s, 1H), 5.18 (ABq, 2H, J=13.8 Hz, Δv=176 Hz), 4.56 (d, 1H, J=7.8 Hz), 4.36 (d, 1H, J=7.8 Hz), 3.05 (q, 1H, J=7.2 Hz), 30 (s, 3H), 2.13 (s, 3H), 2.30–1.90 (overlapping m, 3H), 1.23 (d, 3H, J=7.2Hz), 1.12 (s, 9H).

Example 105
10-(4-benzoylamino-3,5-dimethyl-2-pyridinyl)-methoxy-Ginkgolide B To a solution of 30 mg of 10-(3,5-dimethyl-4-amino-2-pyridinyl)-methoxy Ginkgolide B obtained in Example 103 in 3 ml of tetrahydrofuran was added 12.5 μl of benzoyl chloride followed by stirring at room temperature for 24 hours. The solution was concentrated and subjected to chromatography on silica gel to give 16 mg (45%) of the desired compound.

$^1$H-NMR ($CD_3Cl$); δ 8.31 (s, 1H), 7.94 (d, 2H, J=7.2 Hz), 7.62 (t, 1H, J=7.8 Hz), 7.60 (brs, 1H), 7.54 (t, 1H, J=7.8 Hz), 5.99 (s, 1H), 5.65 (brs, 1H), 5.21 (ABq, 2H, JAB=13.5 Hz, Δv=236 Hz), 4.99 (5, 1H), 4.65 (d, 1H, J=7.5 Hz), 4.45 (d, 1H, J=7.5 Hz), 3.07 (q, 1H, J=6.9 Hz), 2.92 (s, 1H), 2.27 (s, 3H), 2.11 (s, 3H), 2.30–1.90 (overlapping m, 3H), 1.29 (d, 3H, J=6.9 Hz), 1.11 (s, 9H).

Example 106
10-(4-N-benzoyl-N-hydroxyamino-3,5-dimethyl-2-pyridinyl)-methoxy Ginkgolide B To a mixture of 20 mg of 10-(3,5-dimethyl-4-hydroxyamino-2-pyridinyl)-methoxy Ginkgolide B obtained in Example 104 in 2 ml of ethylacetate and 2 ml of saturated sodium carbonate solution was added 8.1 μl of benzoyl chloride by stirring at room temperature. After 3 hours stirring at room temperature, the mixture was extracted with 9 ml of dichloromethane. The solution was dried over anhydrous magnesium sulfate, filtered and concentrated. The residue was subjected to chromatography on silica gel to give 17 mg (70%) of the desired compound.

Example 107
10-(6-chloro-3-pyridinyl)-methoxy-Ginkgolide B

In the same manner as in Example 98, the title compound was prepared using 115 mg of Ginkgolide B and 168 mg of 6-chloro-3-picolyl chloride (87 mg, 59%).

$^1$H-NMR (DMSO-$d_6$); δ 8.40 (d, 1H, J=2.1 Hz), 7.84 (dd, 1H, J=8.3, 2.4 Hz), 7.50 (d, 1H, J=8.4 Hz), 6.41 (s, 1H), 6.15 (s, 1H), 5.61 (d, 1H, J=4.8 Hz), 5.34 (brs, 1H), 5.21 (s, 1H), 5.04 (ABq, 2H, JAB=12.3 Hz, Δv=192.3), 4.60 (d, 1H, J=6.6 Hz), 4.18 (t, 1H, J=5.7 Hz), 2.88 (q, 1H, J=7.2 Hz), 2.15–2.07 (m, 1H), 1.90–1.65 (m, 2H), 1.12 (d, 3H, J=7.2 Hz), 0.99(s, 9H).

Example 108
10-(3-pyridinyl)-methoxy-Ginkgolide B

In the same manner as in Example 98, the title compound was prepared using 200 mg of Ginkgolide B and 250 mg of 3-picolyl chloride (164 mg, 68%).

$^1$H-NMR (DMSO-$d_6$); 8.57 (d, 1H, J=1.2 Hz), 8.50 (dd, 1H, J=4.7, 1.2 Hz), 7.78 (brd, 1H, J=7.8 Hz), 7.38 (dd, 1H, J=7.8, 4.8 Hz), 6.42 (s, 1H), 6.15 (s, 1H), 5.38 (d, 1H, J=5.4 Hz), 5.33 (d, 1H, J=3.3 Hz), 5.23 (s, 1H), 5.05 (ABq, 2H, JAB=123 Hz, Δv=199.5 Hz), 4.60 (d, 1H, J=6.6 Hz), 4.19 (t, 1H, J=5.7 Hz), 2.88 (q, 1H, J=7.2 Hz), 2.15–1.70 (m, 3H), 1.12 (d, 3H, J=7.2 Hz), 0.99 (s, 9H).

Example 109
10-(4-pyridinyl)-methoxy-Ginkgolide B

In the same manner as in Example 98, the title compound was prepared using 200 mg of Ginkgolide B and 240 mg of 4-picolyl chloride (109 mg, 45%).

$^1$H-NMR (DMSO-$d_6$); δ 8.52 (d, 2H, J=5.4 Hz), 8.35 (d, 2H, J=5.4 Hz), 6.42 (s, 1H), 6.16 (s, 1H), 5.74 (d, 1H, J=5.1 Hz), 5.40 (d, 1H, J=3.6 Hz), 5.22 (s, 1H), 5.08 (ABq, 2H, JAB=13.5 Hz, Δv=209 Hz), 4.61 (d, 1H, J=6.6 Hz), 4.21 (t, 1H, J=5.6 Hz), 2.89 (q, 1H, J=6.9 Hz), 2.20–1.70 (m, 3H), 1.12 (d, 3H, J=6.9 Hz), 0.99 (s, 9H).

Example 110 TO 112

In the same manner as in Example 96, the following compounds were prepared.

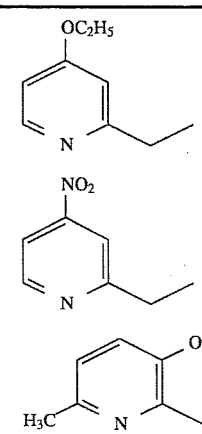

| Example | R$^1$ | R$^2$ | m.p. (°C.) |
|---|---|---|---|
| 110 | OC$_2$H$_5$ | H | |
| 111 | NO$_2$ | H | |
| 112 | O-n-Pr | H | |

Example 113
10-(2-(4-hydroxyaminopyridinyl)-methoxy)-Ginkgolide B

In the same manner as in Example 104, the title compound was prepared using 10-(4-nitro-2-myridinyl)-methoxy Ginkgolide B obtained in Example 111 (85%).

Example 114

10-2-(5-(2-methoxyethoxymethoxy))-pyridinyl)-methoxy Ginkgolide B

In the same manner as in Example 96, the title compound was prepared using Ginkgolide B and 5-(2-methoxyethoxymethoxy)-2-picolyl bromide or the mesylate of 5-(2-methoxyethoxymethoxy)-2-pyridyl carbinol (76%).

Example 115

10-(2-(5-hydroxypyridinyl)-methoxy)-Ginkgolide B

To a solution of 250 mg of the compound obtained in Example 114 in 3 ml of tetrahydrofuran was added 1 ml of c-HCl followed by stirring at room temperature. After 2 hours stirring an room temperature, the mixture was concentrated under reduced pressure.

The residue was subjected to chromatography on silica gel to live 185 mg (89%) of the desired compound.

Example 116

10-(2'-bromoethoxy)-Ginkgolide B

To a solution of 50 mg of Ginkgolide B in 5 ml of tetrahydrofuran was added 16 mg of potassium hydride followed by stirring, in an inert atmosphere, at room temperature for 5 minutes. To the mixture was then added 91 mg of 2-bromoethyltrifluoromethanesulfonate, followed by stirring at room temperature for 1 hour.

The mixture was treated with 0.5 ml of c-HCl at 0° C., diluted with 10 ml of water and extracted with 50 ml of dichloromethane. The solution was washed with 10 ml of water and dried over anhydrous magnesium sulfate. After filtering off, the filtrate was concentrated under reduced pressure.

The residue was subjected to chromatography on silica gel (elution solvent: chloroform/methanol=99/1) to give 61 mg (98%) of the desired compound.

$^1$H-NMR (DMSO); δ 6.43(s, 1H), 6.13 (s, 1H), 5.34 (d, 1H, J=3.0 Hz), 5.13 (s, 1H), 5.03 (d, 1H, J=6.0 Hz), 4.61 (d, 1H, J=6.0 Hz), 4.20 (dt, 2H, J=9.0, 4.5 Hz, Δν=225 Hz), 4.12 (t, 1H, J=6.0 Hz), 3.71 (m, 2H), 2.85 (q, 1H, J=6.9 Hz), 2.14 (dd, 1H, J=13.5, 3.6 Hz), 1.94 (m, 1H), 1.72 (dd, 1H, J=13.5, 3.6 Hz), 1.12 (d, 1H, J=6.9 Hz), 1.02 (s, 9H).

Example 117

10-(2'-iodoethoxy)-Ginkgolide B

To a solution of 1.30 g of 10-(2'-bromoethoxy)-Ginkgolide B obtained in Example 116 in 20 ml of anhydrous acetone was added 0.44 g of sodium iodide followed by stirring at room temperature.

The mixture was stirred at room temperature for 15 hours. After filtering off, the filtrate was concentrated under reduced pressure. The residue was dissolved in 100 ml of ethyl ether, washed with 30 ml of 5% sodium bisulfite solution, dried over anhydrous magnesium sulfate, filtered and concentrated to give 1.20 g (86%) of the desired compound. $^1$H-NMR (CDCl$_3$); δ 5.98(s, 1H), 5.50(d, 1H, J=3.0 Hz), 4.80 (s, 1H), 4.64(d, 1H, J=6.0 Hz), 4.30 (dd, 1H, J=6.0 and 3.0 Hz), 4.29 (m, 2H), 3.38 (t, 2H, J=6.0 Hz), 3.30(d, 1H, J=3.0 Hz), 3.12 (s, 1H), 3.03 (q, 1H, J=6.0 Hz), 2.33 (dd, 1H, J=13.5, 4.5 Hz), 2.16 (td, 1H, J=13.5, 3.0 Hz), 1.93 (dd, 1H, J=13.5, 4.5 Hz), 1.29 (d, 3H, J=6.0 Hz), 1.11(s, 9H).

Example 118

10-(2'-(1"-piperidinyl)-ethoxy)-Ginkgolide B

100 mg of 10-(2'-iodoethoxy)-Ginkgolide B obtained in Example 117 was dissolved in 2 ml of piperidine, and stirred at room temperature for 1 hour. The excess piperidine was removed under reduced pressure. The residue was subjected to chromanography on silica gel to give 57 mg (62%) of the desired compound.

$^1$H-NMR (CDCl$_3$); δ 5.92(s, 1H), 5.52(d, 1H, J=3.0 Hz), 4.72 (s, 1H), 4.57 (d, 1H, J=6.0 Hz), 4.23 (d, 1H, J=6.0 Hz) 4.09 (m, 2H), 3.04 (q, 1H, J=6.0 Hz), 2.67 (m, 3H), 2.28 (m, 4H), 1.99 (m, 2H), 1.64 (m, 4H), 1.48 (m, 2H), 1.29 (d, 3H, J=6.0 Hz), 1.08 (s, 9H).

Example 119

10-(2'-(1"-morpholinyl)-ethoxy)-Ginkgolide B

In the same manned as in Example 118, the title compound was prepared using morpholine (75%).

$^1$H-NMR (CDCl$_3$); δ 7.01(s, 1H), 5.94 (5, 1H), 5.48 (d, 1H, J=3.0 Hz), 4.74 (s, 1H), 4.57 (d, 1H, J=7.5 Hz), 4.21(d, 1H, J=7.5 Hz), 4.14 (ABq, 2H, J=8.1 Hz, Δν=324 Hz), 3.78 (m, 4H), 3.07 (m, 2H), 2.73 (m, 3H), 2.46 (m, 4H), 1.97 (m, 2H), 1.20 (d, 3H, J=7.2 Hz), 1.10 (s, 9H).

Example 120

10-(2'-(1"-(1",2",4"-triazolyl)-ethoxy))-Ginkgolide B

To a stirred solution of 100 mg of 10-(2'-bromoethoxy)-Ginkgolide B obtained in Example 116 in 1.5 ml of dimethylsulfoxide was added 96 mg of 1,2,4-sodiumtriazole at room temperature.

The mixture was stirred at 80° C. for 2 hours, cooled to room temperature, diluted with 10 ml of water and extracted with 50 ml of ethylacetate. The solution was dried over anhydrous magnesium sulfate, filtered, concentrated under reduced pressure. The residue was subjected to chromatography on silica gel to give 72 mg (74%) of the desired compound.

$^1$H-NMR (DMSO); δ 8.37 (s, 1H), 7.98 (s, 1H), 6.40 (brs, 1H), 6.07 (s, 1H), 5.83 (brs, 1H), 5.32 (d, 1H, J=3.0 Hz), 4.97 (5, 1H), 4.63 (d, 1H, J=7.2 Hz), 4.55 (m, 2H), 4.35 (m, 1H), 4.12 (brs, 1H), 3.75 (t, 1H, J=8.2 Hz), 2.83 (q, 1H, J=6.8 Hz), 1.90 (m, 1H), 1.60 (m, 2H), 1.12 (d, 3H, J=6.8 Hz), 0.98 (s, 9H).

Example 121

10-(2'-(1"-piperazinyl)-ethoxy)-Ginkgolide B

To a stirred solution of 100 mg of 10-(2'-iodoethoxy)-Ginkgolide B obtained in Example 117 in 5 ml of pyridine was added mg of piperazine at room temperature. The mixture was stirred at room temperature for 3 hours, concentrated, diluted with 30 ml of saturated sodiumbicarbonate solution and extrated with 50 ml of ethylacetate. The solution was dried over anhydrous magnesium sulfate, filtaed, and concentrated under reduced pressure. The residue was subjected to chromatography on silica gel to give 62 mg (67%) of the desired compound.

¹H), (DMSO); δ 6.87 (brs, 1H), 6.37 (s, 1H), 5.30 (d, 1H, 3.0 Hz), 5.11 (s, 1H), 4.55 (d, 1H, 7.5 Hz), 4.07 (d, 1H, 7.5 Hz), 3.99 (m, 2H), 2.82 (q, 1H, J=6.9 Hz), 2.72 (m, 4H), 2.50 (m, 2H), 2.22 (m, 5H), 1.98 (td, 1H, J=13.0 and 3.0 Hz), 1.76 (dd, 1H, J=13.0 and 3.0 Hz), 1.10 (d, 3H, J=6.9 Hz), 1.00 (s, 9H).

Example 122

10-(2'-(1''-pyrrolidinyl)-ethoxy)-Ginkgolide B

In the same manner as in Example 118, the title compound was prepared using pyrrolidine (75%).

¹H-NMR (CDCl₃); δ 5.92 (s, 1H), 5.50 (d, 1H, J=3.0 Hz), 4.73 (5, 1H), 4.60 (t, 1H, J=9.2 Hz), 4.53 (d, 1H, J=7.5 Hz), 4.21 (d, 1H, J=7.5 Hz), 3.60 (m, 1H), 3.04 (q, 1H, J=6.0 Hz), 2.92 (m, 51H), 2.70 (m, 2H), 2.45 (m, 3H), 2.25 (dd, 1H, J=13.0 and 3.0 Hz), 2.00 (m, 2H), 1.80 (brs, 4H), 1.28 (d, 3H, J=6.0 Hz ), 1.10 (s, 9H).

Compounds which have PAF-antagonistic activity may be used for the treatment and prophylaxis of diseases mediated or effected by PAF. Typical diseases for which the inventive compounds may be used as a therapeutic and prophylactic agent include allergic diseases, asthma, thrombosis, cerebral apoplexy (cerebral hemorrhage, cerebral thrombosis), myocardial infarction (angina pectoris), human disseminated intravascular coagulation syndrome (DIC), thrombophlebitis, glomerular hepatitis, anaphylatic shock, hemorrhagic shock, septic shock, endotoxin shock, rheumatoid arthritis, osteoarthritis, edema, inflammation, cardiovascular disorder, adult respiratory distress syndrome, immune regulation, gastric ulceration, transplant rejection, psoriasis, allergic dermatitis, urticaria, multiple sclerosis, and other conditions in which PAF is implicated.

The inventive ginkgolide B derivatives have potent PAF-antagonistic activity. Accordingly, the new ginkgolide B derivatives may be used in pharmaceutical composition comprising a pharmaceutically effective amount of one of the compounds defined above and a pharmaceutically acceptable carrier. The compounds are effective for the therapy and prophylaxis of diseases mediated or effected by PAF.

The inventive compounds are particularly useful as anti-allergic agents, anti-asthmatic agents, anti-psoriasis agents, anti-anaphylactic shock agents, anti-septic shock agents, an anti-bowel necrosis agents, an adult respiratory distress syndrome agents and anti-transplant rejection agents.

Compounds of formula (I) may be administered orally, topically, parenterally, by inhalation spray or rectally in dosage unit formulations containing conventional non-toxic pharmaceutically acceptable carriers, adjuvants and vehicles.

The term parenteral as used herein includes subcutaneous injections, intravenous injection, intramuscular injection, intrasternal injection or infusion techniques.

The dosage employed depends on the type of disease, the degree of symptom and age. The dosage levels of the compound in the above-indicated compositions may, of course, be varied and may conveniently be between about 0.1% to about 95% of the weight the unit.

When these compounds are administered orally, a dose of 1–50 wt. % is particularly preferred.

For parenteral administration, a dose of 0.1–20 wt. % is particularly preferred.

Pharmaceutical compositions containing compounds of formula (I) may be in any form suitable for oral use, for example, as tablets, troches, lozenges, aqueous or oily suspensions, dispensable powders or granules, emulsion, hard or soft capsules, syrups or elixirs.

The tablets, capsules and the like may also contain a binder, such as lactose, saccharose, sorbitol, mannitol, starch, amylopectin, cellulose or gelatin; excipients, such as dicalcium phosphate; a disintegrating agent, such as corn starch or potato starch; a lubricant, such as magnesium stearate, calcium stearate, sodium stearylfumalate or polyethylenglycol wax. When the dosage unit form is a capsule, it may further contain, in addition to the fatty oil.

These active compounds of formula (I) may also be administered parenterally. A solution or suspension of the active compounds may be prepared in water, optionally mixed with stabilizer or buffering agents. The dosages for parenteral administration are 0.1–10 wt. %, and preferably administered as ampule or vial type.

Dosage levels of about 2 mg to about 1,000 mg (70 kg of body weight, adult) per day are particularly useful for the prevention or treatment of allergic bronchial disease and allergic rheumatoid arthritis. For intravenous injection for treating these conditions, dosage levels of about 1 mg to about 10 mg are particularly preferred.

The compound of the present invention may also be administered directly to the airways, for example, in the form of an aerosol or inhalation by nebulizer, for the treatment of allergic bronchial hyperreactivity. Dosage unit forms will generally contain between about 0.1 mg to about 50 mg of the active ingredient.

Accordingly, the present invention provides pharmaceutical compositions comprising a pharmaceutically effective amount of a compound of formula (I) and a pharmaceutically acceptable carrier. The present invention also provides the pharmaceutical uses of these compounds and compositions, especially for treatment of allergic diseases and inflammatory diseases in humans.

The following examples illustrate the typical pharmaceutical composition. In each case, the active ingredient represents a compounds of general formula (I), which may be substituted by any pharmaceutically effective amount of another compound of general formula (I). [pharmaceutical compositions]

Example 1: Orally administration (Tablet)

| Composition | mg/Tablet | mg/Tablet |
| --- | --- | --- |
| Active Ingredient | 100 | 500 |
| Lactose | 122 | 113 |
| Corn starch/water | 30 | 40 |
| Corn starch | 45 | 40 |
| Magnesium stearate | 3 | 7 |
| Total | 300 | 700 |

Example 2: Parenteral administration

| Composition | mg/vial | mg/vial |
| --- | --- | --- |
| sterile active ingredient powder | 100 | 500 |

*Sterile water may be added to the above composition for intravenous injection.

The compounds of this invention were tested for pharmacological activity as described in the following examples.

Pharmacology Example 1: PAF-induced rabbit platelet aggregation

Blood was collected from the ear artery of a male New Zealand white rabbit and mixed with 3.8% sodium citrate in a 9:1 volume ratio. Platelet rich plasma (PRP) was obtained by centrifugation of the blood at 150 g for 10 min at room temperature. The number of platelets was adjusted to $3 \times 10^8$ platelets/ml with platelet poor plasma. Platelet aggregation was monitored by continuous recording of light transmission in a dual-channel aggregometer (Chrono-Log 560-VS) coupled with a two channel recorder (Chrono-Log 707). Stirred PRP was treated with various concentrations of the test compounds or vehicle (0.5% DMSO) for 2 min and then PAF($5 \times 10^{-9}$M) was added to induce platelet aggregation.

Inhibition values were calculated by comparing the extent of aggregation obtained in the presence of the vehicle alone (0.5% DMSO) and in the presence of a test compound. Log concentration-response curves were generated and the $IC_{50}$ values were determined by regression analysis.

Table 1 lists results from this assay for inhibition of PAF-induced rabbit platelet aggregation for illustrative examples of the compounds of this invention.

TABLE 1

Results for inhibition of PAF-induced rabbit platelet aggregation

| Example | $IC_{50}$(M) |
|---|---|
| Ginkgolide B | $2.58 \times 10^{-7}$ |
| Example 1 | $6.88 \times 10^{-8}$ |
| Example 2 | $7.21 \times 10^{-8}$ |
| Example 3 | $9.47 \times 10^{-8}$ |
| Example 5 | $5.01 \times 10^{-8}$ |
| Example 11 | $1.01 \times 10^{-7}$ |
| Example 14 | $8.58 \times 10^{-8}$ |
| Example 15 | $6.21 \times 10^{-8}$ |
| Example 24 | $4.21 \times 10^{-8}$ |
| Example 25 | $5.71 \times 10^{-8}$ |
| Example 27 | $6.21 \times 10^{-8}$ |
| Example 28 | $3.71 \times 10^{-8}$ |
| Example 30 | $1.21 \times 10^{-7}$ |
| Example 31 | $7.81 \times 10^{-8}$ |
| Example 32 | $6.51 \times 10^{-8}$ |
| Example 35 | $1.01 \times 10^{-7}$ |
| Example 41 | $7.41 \times 10^{-8}$ |
| Example 42 | $4.43 \times 10^{-8}$ |
| Example 43 | $4.67 \times 10^{-8}$ |
| Example 44 | $8.31 \times 10^{-8}$ |
| Example 63 | $6.27 \times 10^{-8}$ |
| Example 75 | $1.16 \times 10^{-7}$ |
| Example 78 | $1.59 \times 10^{-7}$ |
| Example 79 | $1.17 \times 10^{-7}$ |
| Example 80 | $1.14 \times 10^{-7}$ |
| Example 81 | $5.21 \times 10^{-8}$ |
| Example 82 | $5.07 \times 10^{-8}$ |
| Example 83 | $7.17 \times 10^{-8}$ |
| Example 84 | $6.80 \times 10^{-8}$ |
| Example 85 | $3.21 \times 10^{-8}$ |
| Example 86 | $5.01 \times 10^{-8}$ |
| Example 87 | $1.07 \times 10^{-7}$ |
| Example 88 | $4.82 \times 10^{-8}$ |
| Example 89 | $6.21 \times 10^{-8}$ |
| Example 90 | $8.21 \times 10^{-8}$ |
| Example 91 | $9.31 \times 10^{-8}$ |
| Example 92 | $1.02 \times 10^{-7}$ |
| Example 93 | $7.31 \times 10^{-8}$ |
| Example 94 | $1.21 \times 10^{-7}$ |
| Example 95 | $8.71 \times 10^{-8}$ |
| Example 96 | $2.45 \times 10^{-8}$ |
| Example 97 | $3.89 \times 10^{-8}$ |
| Example 98 | $1.31 \times 10^{-7}$ |
| Example 99 | $3.07 \times 10^{-8}$ |
| Example 100 | $5.21 \times 10^{-8}$ |
| Example 101 | $1.02 \times 10^{-7}$ |
| Example 102 | $1.31 \times 10^{-7}$ |
| Example 103 | $8.77 \times 10^{-8}$ |
| Example 104 | $1.10 \times 10^{-7}$ |
| Example 105 | $3.25 \times 10^{-8}$ |
| Example 106 | $4.71 \times 10^{-8}$ |
| Example 107 | $1.57 \times 10^{-7}$ |
| Example 108 | $1.34 \times 10^{-7}$ |
| Example 109 | $1.22 \times 10^{-7}$ |
| Example 110 | $1.57 \times 10^{-7}$ |
| Example 111 | $1.07 \times 10^{-7}$ |
| Example 112 | $1.24 \times 10^{-7}$ |
| Example 113 | $1.11 \times 10^{-7}$ |
| Example 114 | $1.39 \times 10^{-7}$ |
| Example 115 | $1.52 \times 10^{-7}$ |
| Example 116 | $1.13 \times 10^{-7}$ |
| Example 117 | $5.34 \times 10^{-8}$ |
| Example 118 | $4.71 \times 10^{-8}$ |
| Example 119 | $5.41 \times 10^{-8}$ |
| Example 120 | $6.21 \times 10^{-8}$ |
| Example 121 | $5.71 \times 10^{-8}$ |
| Example 122 | $5.61 \times 10^{-8}$ |

Pharmacology Example 2: PAF-induced bronchoconstriction

All experiments utilized male guinea pigs (Hartley strain), weighing 350 to 450 g, that were anesthetized with ethyl carbamate (1.5 g/kg, i.p.). An intratracheal cannula was inserted into trachea and indwelling catheters were inserted into the right carotid artery and left jugular vein. The animals were ventilated with a small animal respirator (UGO BASILE 7025, 70 breaths/min, 1 ml/stroke/100 g). To monitor dead or not, mean arterial pressure was measured continuously with a pressure transducer (Physiological Pressure Transducer, MICRON INSTRUMENT MP-15) connected to an amplifier (COULBOURN INSTRUMENT 572-25) and recorder (COULBOURN INSTRUMENT R14-18). The rate of bronchoconstriction was measured as an increase in lung overflow with a bronchospasm transducer (UGO BASILE 7020) from a side arm off the tracheal cannula, and expressed as a percentage of maximum bronchoconstriction obtained by clamping off the tracheal cannula. Test compounds or vehicle (0.5% DMSO) were administered through the cannula into the jugular vein and PAF (100 ng/kg, i.v.) was administered. Bronchoconstriction response was compared to that obtained with control group treated with vehicle. Percent inhibition was calculated for each dose. Log dose-response curves were generated and the ID50 values were determined by regression analysis, and the results are presented in Table 2.

Table 2: Results for inhibition of PAF-induced bronchoconstriction in the guinea pig.

| Example | Dose(mg/kg) | % inhibition | $ID_{50}$(mg/kg) |
|---|---|---|---|
| Ginkgolide B | 2.00 | 100 | 0.60 |
|  | 1.00 | 64 |  |
|  | 0.50 | 38 |  |
| 96 | 0.04 | 96 | 0.023 |
|  | 0.02 | 26 |  |
|  | 0.01 | 17 |  |

Pharmacology Example 3: Ag-induced bronchoconstriction

All experiments utilized male guinea pigs (Hartley strain), weighing 350 to 500 g. The animal was passively sensitized with rabbit anti-chicken egg albumin (1.3 mg/kg), 17–24 hrs before ovaibumin challenge. Passively sensitized animals were anesthetized with ethyl carbamate 1.5 g/kg, i.p.). An intratracheal cannula was inserted into trachea and indwelling catheters were inserted into the right carotid artery and left jugular vein. The animals were ventilated with a small animal respirator (UGO BASILE 7025, 70 breaths/min, 1 ml/stroke/100 g). To monitor dead or not, mean arterial pressure was measured continuously with a pressure transducer (Physiological Pressure Transducer, MICRON INSTRUMENT MP-15) connected to an amplifier (COULBOURN INSTRUMENT 572-25) and recorder (COULBOURN INSTRUMENT R14-18). The rate of bronchoconstriction was measured as an increase in lung overflow with a bronchospasm transducer (UGO BASILE 7020) from a side arm off the tracheal cannula, and expressed as a percentage of maximum broncoconstriction obtained by clamping off the tracheal cannular. Test compounds or vehicle (0.5% DMSO) were administered through the cannula into the jugular vein and ovalbumin (1.0 mg/kg, i.v.) was administered 10 minutes later. Bronchoconstriction response was compared to that obtained with control group treated with vehicle. Percent inhibition was calculated for each dose. If necessary, log dose-response curves were generated and the $ID_{50}$ values were determined by regression analysis. The results are presented in Table 3.

TABLE 3

Results for inhibition of Ag-induced bronchoconstriction in the guinea pig.

| Example | Dose(mg/kg) | % inhibition | $ID_{50}$(mg/kg) |
| --- | --- | --- | --- |
| Ginkgolide B | 1.0 | 82 | 0.83 |
| | 0.5 | 42 | |
| | 0.1 | 10 | |
| 82 | 1.0 | 100 | 0.09 |
| | 0.5 | 94 | |
| | 0.1 | 60 | |
| 96 | 1.0 | 100 | 0.10 |
| | 0.5 | 97 | |
| | 0.1 | 50 | |
| 97 | 1.0 | 100 | 0.42 |
| | 0.5 | 68 | |
| | 0.1 | 30 | |
| 99 | 1.0 | 100 | 0.31 |
| | 0.5 | 73 | |
| | 0.1 | 42 | |
| 103 | 1.0 | 97 | 0.48 |
| | 0.5 | 62 | |
| | 0.1 | 10 | |
| 115 | 1.0 | 100 | 0.08 |
| | 0.5 | 100 | |
| | 0.1 | 65 | |

Pharmacology Example 4: The aeroallergen-induced bronchial infiltration of eosinophils in the bronchoalveolar lavage fluid.

Adult, male Hartley-strain guinea pigs weighing 492–735 g were sensitized by intraperitoneal injection of 10 μg ovalbumin (OA) mixed in 100-mg aluminum hydroxide. And guinea pigs were pretreated with pyrilamine (1.0 mg/kg) intraperitoneally 30 min. before aeroallergen challenge. Individual guinea pigs were placed in a two-liter glass chamber and exposed to a five aerosol of OA solution (0.5 mg/ml in saline containing 0.02% antifoal emulsion for a period of 10 min.).

4 hours after aero allergen challenge, the guinea pigs received either vehicle or compounds suspended in 1% acacia by oral garage.

24 hours after aero allergen challenge, the animals were euthanized with an i.p. overdose of pentobarbital sodium (100 mg/kg). The abdominal cavity was opened, and the animal was exsaguinated by cutting the abdominal aorta. A midline incision was made through the rib cage, exposing the heart and lungs.

The trachea was cannulated with an 18-gauge stainless steel feeding tube; 20 ml/kg of prewarmed (37° C.) physiological saline was instilled and the BALF was gently withdrawn.

BALF (amounting to 60–80% of the saline infused) was transferred to a 10 ml vacutainer containing 0.10 ml of 15% EDTA solution and centrifugated at 2400 rpm for 10 min.

The supernatant was poured off, and the cell pellet was suspended in physiological saline equal to the ratio of BALF recovered (ml) and physiological saline instilled in the lungs (ml), multiplied by two.

The eosinophils in BALF were counted by Unopette Test 5877.

The mean numbers of eosinophils±SEM in the BALF of compound-treated animals and corresponding control "vehicle"-treated animals were compared by Student's t-test. A P value of 0.05 or less was considered significant. Table 4 lists results from this assay for inhibition of bronchial eosinophilia for illustrative examples of this invention.

TABLE 4

Results for inhibition of bronchial eosinophilia in the guinea pig.

| Example | Dose mg/kg, p.o., + 4h | Numbers of Guinea pig. | Eosinophils $10^3$ cells/ml BALF (Mean ± SEM) | % Inhibition |
| --- | --- | --- | --- | --- |
| vehicle only | — | 10 | 927 ± 131 | — |
| Ginkgolide B | 30 | 4 | 1148 ± 305 | 0 |
| 82 | 30 | 10 | 616 ± 145 | 34 |
| 96 | 30 | 7 | 641 ± 134 | 31 |

*P < 0.05 as compared to control.

Pharmacology Example 5: PAF induced Lethality in Mice

PAF given I.V. (10 μg/kg) to mice causes an immediate hypotensive shock leading to death in 1 hour or less. Compounds were given intraperitoneally (dose of compounds : 10 mg/kg) at 2 minutes before the PAF challenge. Animals alive after 2 hours were counted and the activity of test compounds expressed as % survival corrected for any control (saline treated) animals which survived the PAF challenge. The results are presented in Table 5.

TABLE 5

Results for protection of PAF induced Lethality in Mice

| Example | Survival rate (%) |
| --- | --- |
| control | 0 |
| 82 | 100 |
| 96 | 100 |
| 115 | 100 |

What is claimed is:

1. A compound of formula (I):

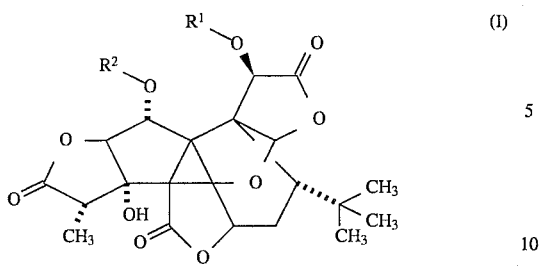

(I)

wherein,

R² represents hydrogen or a R¹ group; and
R¹ represents —A—Ar, —A—Z—Ar,

—C—Ar,

—SO₂—Ar, —A—Het, or —A—NR⁴R⁵, in which A represents an alkylene group having 1 to 8 carbon atoms, which is unsubstituted or substituted by a straight or branched alkyl chain group having 1 to 5 carbon atoms; Z represents carbon, oxygen, sulfur or nitrogen; Ar represents a phenyl group, a pyridyl group, a naphthyl group, a pyrimidyl group, or a quinolyl group, each of which may be unsubstituted or substituted by one to five substituents selected from the group consisting of hydrogen, halogen, a hydroxy group, a carboxylic acid group, an alkyl group having 1 to 10 carbon atoms, an alkenyl group having 1 to 10 carbon atoms, an alkynyl group having 1 to 10 carbon atoms, a haloalkyl group having 1 to 10 carbon atoms, an alkoxy group having 1 to 10 carbon atoms, an alkenyloxy group having 1 to 10 carbon atoms, an alkynyloxy group having 1 to 10 carbon atoms, a haloalkoxy group having 1 to 10 carbon atoms, a phenyl group, a phenoxy group, an aralkyl group, an aralkyloxy group, a substituted phenyl group, a substituted phenoxy group, a substituted aralkyl group, a substituted aralkyloxy group, —COR⁴, —COR⁴, —CONR⁴R⁵, —CO₂R⁴, —NHCOR⁴, —NH(OH), —N(OH)COR⁴, —CHOR⁴, —OCH₂CO₂R⁴, —CH₂SR⁴, —CH₂NR⁴R⁵, —SR⁴, —OSR⁴, —O₂NR⁴R⁵, —NR⁴R⁵, —NR⁴SO₂R⁵, in which R⁴ and R⁵ are the same or different and each is hydrogen, an alkyl group having 1 to 10 carbon atoms or a cycloalkyl group having 3 to 10 carbon atoms, —SCX₃ in which X is a halogen, —CN, —NO₂ and —Z—A—Z'— in which Z and A are as defined above and Z' represents carbon, oxygen, sulfur, or nitrogen; Het. represents a cyclic saturated or unsaturated heterocyclic group having one or more nitrogen, oxygen, and/or sulfur atoms.

2. A compound according to claim 1, wherein
R² represents a hydrogen atom or a R¹ group; and
R¹ represents —A—Ar, —A—Z—Ar, —CO—Ar, —SO₂—Ar, —A—Het, or —A—NR⁴R⁵, in which A represents an alkylene group having 1 to 8 carbon atoms selected from methylene, ethylene, trimethylene, tetramethylene, pentamethylene, hexamethylene, heptamethylene and octamethylene or an alkylene group having 1 to 8 carbon atoms which is substituted by a straight or branched chain alkyl group having 1 to 5 carbon atoms selected from methylmethylene, propylene, methyltrimethylene, dimethylethylene, dimethyltetramethylene, ethylethylene and dimethyltrimethylene; Z represents carbon, oxygen sulfur or nitrogen;

Het. represents a saturated or unsaturated heterocyclic group having one or more nitrogen, oxygen and sulfur atoms selected from morpholinyl, piperidinyl, piperazinyl, triazolyl, imidazolyl, pyrrolidyl, thiazolidinyl and furanyl; Ar represents a phenyl group, a pyridyl group, a naphthyl group, a pyrimidyl group, or a quinolyl group, each of which may be unsubstituted or substituted by one to five substituents selected from hydrogen; a halogen selected from fluoro, chloro, bromo and iodo; a hydroxy group; a carboxylic acid group; an alkyl group having 1 to 10 carbon atoms selected from methyl, ethyl, n-propyl, isopropyl, n-butyl, isobutyl, tert-butyl, n-pentyl, isopentyl, 1-methylbutyl, n-hexyl, 1-methylpentyl, n-heptyl, 4-methylhexyl, 1-ethylpentyl, 1,4-dimethylpentyl, n-octyl, 6-methylheptyl and 2-ethylhexyl; an alkenyl group having 1 to 10 carbon atoms selected from vinyl, allyl, 3-pentenyl and 1-hexenyl; an alkynyl group having 1 to 10 carbon atoms; a haloalkyl group having 1 to 10 carbon atoms selected from fluoromethyl, chloromethyl, bromomethyl, iodomethyl, trifluoromethyl, trifluoroethyl, trifluoropropyl, trifluoromethylethyl and trifluoromethylpropyl; an alkoxy group having 1 to 10 carbon atoms selected from methoxy, ethoxy, n-propoxy, isopropoxy, n-butoxy, isobutoxy, tert-butoxy, n-pentyloxy, isopentyloxy, n-hexyloxy, n-heptyloxy, 1-propylbutoxy, n-octyloxy, 5-methylhexyloxy, 2-ethylhexyloxy and 1,6-dimethylhexyloxy; an alkenyloxy group having 1 to 10 carbon atoms: an alkynyloxy group having 1 to 10 carbon atoms; a haloalkoxy group having 1 to 10 carbon atoms; a phenyl group; a phenoxy group; an aralkyl group selected from benzyl, 1-phenylethyl, 2-phenylethyl, 3-phenylpropyl, and 4-phenylbutyl; an aralkyloxy group selected from benzyloxy, 2-phenylethoxy, 3-phenylpropoxy and 4-phenylbutoxy; a substituted phenyl group selected from 2-chlorophenyl, 2-bromophenyl, 2-fluorophenyl, 2-iodophenyl, 3-fluorophenyl, 2,3-dichlorophenyl, 4-hydroxyphenyl, 2-methylphenyl, 4-methylphenyl, 3-ethylphenyl, 4-propylphenyl, 4-isopropylphenyl, 4-butylphenyl, 4-tert-butylphenyl, 4-pentylphenyl, 2,4-dimethylphenyl, 2-trifluoromethylphenyl, 3-trifluoromethylphenyl, 2-methoxyphenyl, 4-methoxyphenyl, 3-ethoxyphenyl, 2-propoxyphenyl, 4-butoxyphenyl and 2,4-dimethoxyphenyl; a substituted phenoxy group selected from 3,4,5-trimethoxyphenoxy, 2-chlorophenoxy, 2,3-dichlorophenoxy, 4-hydroxyphenoxy, 2-methoxyphenoxy, 4-butylphenoxy and 2,4-dimethylphenoxy; a substituted aralkyl group selected from chlorobenzyl, bromobenzyl, fluorobenzyl, iodobenzyl, dichlorobenzyl, dibromobenzyl, difluorobenzyl, hydroxybenzyl, methylbenzyl, halomethylbenzyl, methoxybenzyl and trimethoxybenzyl; a substituted aralkyloxy group selected from chlorobenzyloxy, dimethylbenzyloxy, trifluoromethylbenzyloxy and trimethoxybenzyloxy; —COR⁴; —CONR⁴R⁵; —CO₂R⁴; —NHCOR⁴; —N(OH)H; —N(OH)COR⁴; —CH₂OR⁴; —OCH₂CO₂R⁴; —CH₂SR⁴; —CH₂NR⁴R ⁵; —SR⁴; —OSR⁴; —SO₂NR⁴R⁵; —NR⁴R⁵; —NR⁴SO₂R⁴, in which R⁴ and R ⁵ are the same or different and each is hydrogen, an alkyl group having 1 to 10 carbon atoms or a cycloalkyl group having 3 to 10 carbon atoms; —SCX₃, in which X represents halogen; —CN; —NO₂; or cyclic linked substituent, —Z—A—Z'—, in which Z and A are as defined above, and Z' represents carbon, oxygen, sulfur or nitrogen, selected from —OCH₂O—, —OCH₂CH₂O—, —OCH₂CH₂CH₂O—, —OCH₂CH₂N—, —NCH₂CH₂N—, —OCH₂CH₂—, —NCH₂CH₂—, —NCH₂CH₂CH₂SCH₂S—, —SCH₂CH₂S—, —SCH₂—, —SCH₂CH₂— and —SCH₂CH₂CH₂—.

3. A compound according to claim 1, wherein

R₂ is hydrogen; and

R¹ is —CH₂—Ar, —CH₂CH₂—Ar, —CH₂CH₂CH₂—Ar, —CH₂O—Ar, —CH₂CH₂CH₂O—Ar,

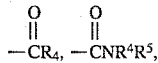

or —SO₂—Ar, in which Ar is a phenyl group, a pyridyl group, a pyrimidyl group or a quinolyl group, each of which is unsubstituted or substituted by one to five substituents selected from the group consisting of hydrogen, halogen, a hydroxy group, an alkyl group having 1 to 10 carbon atoms, a haloalkyl group having 1 to 10 carbon atoms, an alkoxy group having 1 to 10 carbon atoms, a haloalkoxy group having 1 to 10 carbon atoms, a phenyl group, a phenoxy group, an aralkyl group, anaralkyloxy group, $$-CR_4, -CNR^4R^5,$$

—CO₂R⁴, —CH₂OR⁴, —NR⁴R⁵, —CH₂NR⁴R⁵, —CN, —NO₂ and —Z—A—Z'—.

4. A compound according to claim 1, wherein said compound is selected from the group consisting of
10-benzyloxy-Ginkgolide B,
10-(2',4'-dichlorobenzyloxy)-Ginkgolide B,
10-(4'-chlorobenzyloxy)-Ginkgolide B,
10-(4'-methoxybenzyloxy)-Ginkgolide B,
10-(3',4',5'-trimethoxybenzyloxy)-Ginkgolide B,
10-(2'-methylbenzyloxy)-Ginkgolide B,
1,10-bis(2'-methylbenzyloxy)-Ginkgolide B,
10-(4'-methylbenzyloxy)-Ginkgolide B,
10-(3'-phenoxypropoxy)-Ginkgolide B,
10-(2'-phenylethoxy)-Ginkgolide B,
10-(3',4',5'-trimethoxybenzoyloxy)-Ginkgolide B,
10-(4'-phenylbenzyloxy)-Ginkgolide B,
10-piperonyloxy-Ginkgolide B,
10-(2',3',4',5',6'-pentafluorobenzyloxy)-Ginkgolide B,
10-(2',4'-difluorobenzyloxy)-Ginkgolide B,
10-(4'-fluorobenzyloxy)-Ginkgolide B,
10-(2'-fluorobenzyloxy)-Ginkgolide B,
10-benzoyloxy-Ginkgolide B,
1-benzoyloxy-Ginkgolide B,
1,10-bis (2',4'-dichlorobenzyloxy)-Ginkgolide B,
10-(3'-trifluoromethylbenzyloxy)-Ginkgolide B,
10-benzenesulfonyloxy-Ginkgolide B,
10-(3'-methoxybenzyloxy)-Ginkgolide B,
10-(4'-trifluoromethylbenzyloxy)-Ginkgolide B,
1,10-bis (4'-trifluoromethylbenzyloxy)-Ginkgolide B,
10-(4'-hydroxybenzyloxy)-Ginkgolide B,
10-(4'-ethoxybenzyloxy)-Ginkgolide B,
10-(3'-bromobenzyloxy)-Ginkgolide B,
10-(4'-iodobenzyloxy)-Ginkgolide B,
10-(2',3',4'-trihydroxybenzyloxy)-Ginkgolide B,
10-(2'-iodobenzyloxy)-Ginkgolide B,
10-(2'-hydroxybenzyloxy)-Ginkgolide B,
10-(3'-iodobenzyloxy)-Ginkgolide B,
10-(3'-hydroxybenzyloxy)-Ginkgolide B,
10-(2'-bromobenzyloxy)-Ginkgolide B,
10-(3',4'-dihydroxybenzyloxy)-Ginkgolide B,
10-(4'-bromobenzyloxy)-Ginkgolide B,
10-(2'-chlorobenzyloxy)-Ginkgolide B,
10-(3'-chlorobenzyloxy)-Ginkgolide B,
10-(2',4'-dibromobenzyloxy)-Ginkgolide B,
10-(2',3',4',5',6'-pentachlorobenzyloxy)-Ginkgolide B,
10-(2',3',4',5',6'-pentabromobenzyloxy)-Ginkgolide B,
10-(2',3',4',5',6'-pentaiodobenzyloxy)-Ginkgolide B,
10-(2'-methoxybenzyloxy)-Ginkgolide B,
10-(3'-methoxybenzyloxy)-Ginkgolide B,
10-(2'-ethoxybenzyloxy)-Ginkgolide B,
10-(3'-ethoxybenzyloxy)-Ginkgolide B,
10-(2'-propoxybenzyloxy)-Ginkgolide B,
10-(2'-propoxybenzyloxy)-Ginkgolide B,
10-(4'-propoxybenzyloxy)-Ginkgolide B,
10-(2'-isopropoxybenzyloxy)-Ginkgolide B,
10-(3'-isopropoxybenzyloxy)-Ginkgolide B,
10-(4'-isopropoxybenzyloxy)-Ginkgolide B,
10-(4'-methylbenzyloxy)-Ginkoglide B,
10-(2'-ethylbenzyloxy)-Ginkgolide B,
10-(3'-ethylbenzyloxy)-Ginkgolide B,
10-(4'-ethylbenzyloxy)-Ginkgolide B,
10-(2'-propylbenzyloxy)-Ginkgolide B,
10-(3'-propylbenzyloxy)-Ginkgolide B,
10-(2'-bromoethoxy)-Ginkgolide B,
10-(2'-iodoethoxy)-Ginkgolide B,
10-(2'-(1"-piperidinyl)-ethoxy)-Ginkgolide B,
10-(2'-(1"-morphorinyl)-ethyl)-Ginkgolide B,
10-(2'-(1"-(1",2",4"-triazolyl)-ethoxy))-Ginkgolide B,
10-(2'-(1"-piperazinyl))-Ginkgolide B,
10-(2'-(1"-pyrrolidinyl)-ethoxy)-Ginkgolide B,
10-(3,5-dimethyl-2-pyridinyl)-methoxy-Ginkgolide B,
10-(4-methoxy-3,5-dimethyl-2-pyridinyl)-methoxy-Ginkgolide B,
10-(3,5-dimethyl-4-nitro-2-pyridinyl)-methoxy-Ginkgolide B,
10-(2-pyridinyl)-methoxy-Ginkgolide B,
10-(5-butyl-2-pyridinyl)-methoxy-Ginkgolide B,
10-(2-pyridinyl)-ethoxy-Ginkgolide B,
10-(2-quinolinyl)-methoxy-Ginkgolide B,
10-(3,5-dimethyl-4-amino-2-pyridinyl)-methoxy-Ginkgolide B,
10-(3,5-dimethyl-4-nitro-2-pyridinyl)-methoxy-Ginkgolide B,
10-(3,5-dimethyl-4-hydroxy-2-pyridinyl)-methoxy-Ginkgolide B,
10-(3,5-dimethyl-4-hydroxyamino-2-pyridinyl)-methoxy-Ginkgolide B,
10-(4-benzoylamino-3,5-dimethyl-2-pyridinyl)-methoxy-Ginkgolide B,
10-(4-N-benzoyl-N-hydroxyamino-3,5-dimethyl-2-pyridinyl-methoxy-Ginkgolide B,
10-(6-chloro-3-pyridinyl)-methoxy-Ginkgolide B,
10-(3-pyridinyl)-methoxy-Ginkgolide B,
10-(4-pyridinyl)-methoxy-Ginkgolide B,
10-(2-(4-ethoxypyridinyl))-methoxy-Ginkgolide B,
10-(2-(4-nitropyridinyl))-methoxy-Ginkgolide B,
10-(2-(6-methyl-3-propoxypyridinyl))-methoxy-Ginkgolide B,
10-(2-(4-hydroxyaminopyridinyl))-methoxy-Ginkgolide B,
10-(2-(5-methoxyethoxymethoxypyridinyl))-methoxy-Ginkgolide B,
10-(2-(5-hydroxypyridinyl))-methoxy-Ginkgolide B,
10-(4'-propylbenzyloxy)-Ginkgolide B,
10-(2'-isopropylbenzyloxy)-Ginkgolide B,
10-(3'-isopropylbenzyloxy)-Ginkgolide B,
10-(4'-isopropylbenzyloxy)-Ginkgolide B,
10-(2'-butylbenzyloxy)-Ginkgolide B,
10-(3'-butylbenzyloxy)-Ginkgolide B, 10-(4'-butylbenzyloxy)-Ginkgolide B,
10-(4'-pentylbenzyloxy)-Ginkgolide B,
10-(2',3'-dihydroxybenzyloxy)-Ginkgolide B,
10-(2',4'-dihydroxybenzyloxy)-Ginkgolide B,
10-(2',5'-dihydroxybenzyloxy)-Ginkgolide B,
10-(2',6'-dihydroxybenzyloxy)-Ginkgolide B,
10-(3',5'-dihydroxybenzyloxy)-Ginkgolide B,
10-(3',6'-dihydroxybenzyloxy)-Ginkgolide B,
10-(3',4',5'-trihydroxybenzyloxy)-Ginkgolide B,
10-(2'-vinylbenzyloxy)-Ginkgolide B,
10-(3'-vinylbenzyloxy)-Ginkgolide B,
10-(4'-vinylbenzyloxy)-Ginkgolide B,
10-(2'-allylbenzyloxy)-Ginkgolide B,
10-(2'-trifluoromethylbenzyloxy)-Ginkgolide B,
10-(2'-trichloromethylbenzyloxy)-Ginkgolide B,
10-(3'-trichloromethylbenzyloxy)-Ginkgolide B,
10-(4'-trichloromethylbenzyloxy)-Ginkgolide B,
10-(2'-tribromomethylbenzyloxy)-Ginkgolide B,
10-(3'-tribromomethylbenzyloxy)-Ginkgolide B,
10-(4'-tribromomethylbenzyloxy)-Ginkgolide B,
10-(2'-fluoromethylbenzyloxy)-Ginkgolide B,
10-(3'-allylbenzyloxy)-Ginkgolide B,
10-(4'-allylbenxyloxy)-Ginkgolide B,
10-(3'-fluoromethylbenzyloxy)-Ginkgolide B,
10-(4'-fluoromethylbenzyloxy)-Ginkgolide B,
10-(2'-chloromethylbenzyloxy)-Ginkgolide B,
10-(3'-chloromethylbenzyloxy)-Ginkgolide B,
10-(4'-chloromethylbenzyloxy)-Ginkgolide B,
10-(2'-bromomethylbenzyloxy)-Ginkgolide B,
10-(3'-bromomethylbenzyloxy)-Ginkgolide B,
10-(4'-bromomethylbenzyloxy)-Ginkgolide B,
10-(2'-fluoromethoxybenzyloxy)-Ginkgolide B,
10-(3'-fluoromethoxybenzyloxy)-Ginkgolide B,
10-(4'-fluoromethoxybenzyloxy)-Ginkgolide B,
10-(2'-chloromethoxybenzyloxy)-Ginkgolide B,
10-(3'-chloromethoxybenzyloxy)-Ginkgolide B,
10-(4'-chloromethoxybenzyloxy)-Ginkgolide B,
10-(2'-bromomethoxybenzyloxy)-Ginkgolide B,
10-(3'-bromomethoxybenzyloxy)-Ginkgolide B,
10-(4'-bromomethoxybenzyloxy)-Ginkgolide B,
10-(2'-trifluoromethoxybenzyloxy)-Ginkgolide B,
10-(3'-trifluoromethoxybenzyloxy)-Ginkgolide B,
10-(4'-trifluoromethoxybenzyloxy)-Ginkgolide B,
10-(2'-trichloromethoxybenzyloxy)-Ginkgolide B,
10-(3'-trichloromethoxybenzyloxy)-Ginkgolide B,
10-(4'-trichloromethoxybenzyloxy)-Ginkgolide B,
10-(2'-tribromomethoxybenzyloxy)-Ginkgolide B,
10-(3'-tribromomethoxybenzyloxy)-Ginkgolide B,
10-(4'-tribromomethoxybenzyloxy)-Ginkgolide B,
10-(2'-phenoxybenzyloxy)-Ginkgolide B,
10-(2'-benzylbenzyloxy)-Ginkgolide B,
10-(3'-phenoxybenzyloxy)-Ginkgolide B,
10-(3'-benzylbenzyloxy)-Ginkgolide B,
10-(4'-phenoxybenzyloxy)-Ginkgolide B,
10-(4'-benzylbenzyloxy)-Ginkgolide B,
10-(1'-phenethoxy)-Ginkgolide B,
10-(3'-phenpropoxy)-Ginkgolide B,
10-(4'-phenbutoxy)-Ginkgolide B,
10-(4'-(2"-phenethyl)-benzyloxy)-Ginkgolide B,
10-(4'-(1"-phenethyl)-benzyloxy)-Ginkgolide B,
10-(4'-(3"-phenpropyl)-benzyloxy)-Ginkgolide B,
10-(4'-(4"-phenbutyl)-benzyloxy)-Ginkgolide B,
10-(4'-(2"-chlorophenyl)-benzyloxy)-Ginkoglide B,
10-(4'-(2"-bromophenyl)-benzyloxy)-Ginkgolide B,
10-(4'-(2"-fluorophenyl)-benzyloxy)-Ginkgolide B,
10-(4'-(2"-bromophenyl)-benzyloxy)-Ginkgolide B,
10-(4'-(2"-iodophenyl)-benzyloxy)-Ginkgolide B,
10-(4'-(3"-fluorophenyl)-benzyloxy)-Ginkgolide B,
10-(4'-(2",3"-dichlorophenyl)-benzyloxy)-Ginkgolide B,
10-(4'-(4"-hydroxyphenyl)-benzyloxy)-Ginkgolide B,
10-(4'-(2"-methylphenyl)-benzyloxy)-Ginkgolide B,
10-(4'-(4"-methylphenyl)-benzyloxy)-Ginkgolide B,
10-(4'-(3"-ethylphenyl)-benzyloxy)-Ginkgolide B,
10-(4'-(4"-propylphenyl)-benzyloxy)-Ginkgolide B,
10-(4'-(4"-isopropylphenyl)-benzyloxy)-Ginkgolide B,
10-(4'-(4"-butylphenyl)-benzyloxy)-Ginkgolide B,
10-(4'-(4"-pentylphenyl)-benzyloxy)-Ginkgolide B,
10-(4'-(2",4"-dimethylphenyl)-benzyloxy)-Ginkgolide B,
10-(4'-(2"-trifluoromethylphenyl)-benzyloxy)-Ginkgolide B,
10-(4'-(2"-methoxyphenyl)-benzyloxy)-Ginkgolide B,
10-(4'-(3"-methoxyphenyl)-benzyloxy)-Ginkgolide B,
10-(4'-(4"-methoxyphenyl)-benzyloxy)-Ginkgolide B,
10-(4'-(3"-ethoxyphenyl)-benzyloxy)-Ginkgolide B,
10-(4'-(2"-propoxyphenyl)-benzyloxy)-Ginkgolide B,
10-(4'-(4"-butoxyphenyl)-benzyloxy)-Ginkgolide B,
10-(4'-(2",4"-dimethoxyphenyl)-benzyloxy)-Ginkgolide B,
10-(4'-(3",4",5"-trimethoxyphenoxy)-benzyloxy)-Ginkgolide B,
10-(4'-(2"-chlorophenoxy)-benzyloxy)-Ginkgolide B,
10-(4'-(2",3"-dichlorophenoxy)-benzyloxy)-Ginkgolide B,
10-(4'-(4"-hydroxyphenoxy)-benzyloxy)-Ginkgolide B,
10-(4'-(2"-methoxyphenoxy)-benzyloxy)-Ginkgolide B,
10-(4'-(4"-butylphenoxy)-benzyloxy)-Ginkgolide B,
10-(4'-(2",4"-dimethoyphenoxy)-benzyloxy)-Ginkgolide B,
10-(4'-(4"-chlorobenzyl)-benzyloxy)-Ginkgolide B,
10-(4'-(4"-bromobenzyl)-benzyloxy)-Ginkgolide B,
10-(4'-(4"-fluorobenzyl)-benzyloxy)-Ginkgolide B,
10-(2'-nitrobenzyloxy)-Ginkgolide B,
10-(3'-nitrobenzyloxy)-Ginkgolide B,
10-(4'-nitrobenzyloxy)-Ginkgolide B,
10-(2'-cyanobenzyloxy)-Ginkgolide B,
10-(3'-cyanobenzyloxy)-Ginkgolide B,
10-(4'-cyanobenzyloxy)-Ginkgolide B,
10-(2'-aminobenzyloxy)-Ginkgolide B,
10-(3'-aminobenzyloxy)-Ginkgolide B,
10-(4'-aminobenzyloxy)-Ginkgolide B,
10-(2'-dimethylaminobenzyloxy)-Ginkgolide B,
10-(3'-dimethylaminobenzyloxy)-Ginkgolide B,
10-(4'-dimethylaminobenzyloxy)-Ginkgolide B,
10-(3',4'-dihydroxybenzyloxy)-Ginkgolide B,
10-(3,5-dimethyl-4-hydroxybenzyloxy)-Ginkgolide B,
10-(3,5-di-tert-butyl-4-hydroxybenzyloxy)-Ginkgolide B,
10-(4-hydroxy-3-methoxybenzyloxy)-Ginkgolide B,
10-(3,5-dimethoxy-4-hydroxybenzyloxy)-Ginkgolide and
10-(3-amino-4-hydroxy-5-methyl-benzyloxy)-Ginkgolide B.

5. A pharmaceutical composition comprising a compound of formula (I) as claimed in claim 1 and a pharmaceutically acceptable carrier.

6. A pharmaceutical composition for the prevention or treatment of PAF-induced diseases or allergen-induced diseases comprising a compound of formula (I) as claimed in claim 1.

7. A method for treating asthma in a mammal which comprises administering to the mammal an antiasthmatic amount of a compound as claimed in claim 1.

8. A method for treating anaphylatic and septic shock in a mammal which comprises administering to said mammal an effective amount of a compound as claimed in claim 1.

9. A method for treating psoriasis in a mammal which comprises administering to the mammal an effective amount of a compound as claimed in claim 1.

10. A method for treating bowel necrosis in a mammal which comprises administering to the mammal an effective amount of a compound as claimed in claim 1.

11. A method for treating adult respiratory distress syndrome in a mammal which comprises administering to the mammal an effective amount of a compound as claimed in claim 1.

12. A method for treating transplant rejection in a mammal which comprises administering to the mammal an effective amount of a compound as claimed in claim 1.

13. A compound of formula (I):

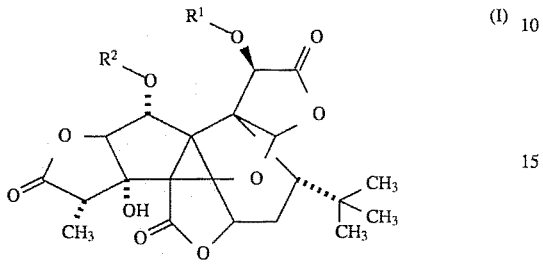

wherein, $R^2$ represents hydrogen or a $R^1$ group; and
$R^1$ represents —A—Ar, —A—Z—Ar,

or —$SO_2$—Ar, in which A represents an alkylene group having 1 to 8 carbon atoms, which is unsubstituted or substituted by a straight or branched alkyl chain group having 1 to 5 carbon atoms; Z represents carbon, oxygen, sulfur or nitrogen; Ar represents a phenyl group, a pyridyl group, a naphthyl group, a pyrimidyl group, or a quinolyl group, each of which may be unsubstituted or substituted by one to five substituents selected from the group consisting of hydrogen, halogen, a hydroxy group, a carboxylic acid group, an alkyl group having 1 to 10 carbon atoms, an alkenyl group having 1 to 10 carbon atoms, an alkynyl group having 1 to 10 carbon atoms, a haloalkyl group having 1 to 10 carbon atoms, an alkoxy group having 1 to 10 carbon atoms, an alkenyloxy group having 1 to 10 carbon atoms, an alkynyloxy group having 1 to 10 carbon atoms, a haloalkoxy group having 1 to 10 carbon atoms, a phenyl group, a phenoxy group, an aralkyl group, an aralkyloxy group, a substituted phenyl group, a substituted phenoxy group, a substituted aralkyl group, a substituted aralkyloxy group, —$COR^4$, —$CONR^4R^5$, —$CO_2R^4$, —$NHCOR^4$, —NH(OH), —N(OH)$COR^4$, —$CHOR^4$, —$OCH_2CO_2R^4$, —$CH_2SR^4$, —$CH_2NR^4R^5$, —$SR^4$, —$OSR^4$, —$O_2NR^4R^5$, —$NR^4R^5$, —$NR^4SO_2R^5$, in which $R^4$ and $R^5$ are the same or different and each is hydrogen, an alkyl group having 1 to 10 carbon atoms or a cycloalkyl group having 3 to 10 carbon atoms, —$SCX_3$ in which X is a halogen, —CN, —$NO_2$ and —Z—A—Z'— in which Z and A are as defined above and Z' represents carbon, oxygen, sulfur, or nitrogen.

14. A compound according to claim 13, wherein
$R^2$ represents a hydrogen atom or a $R^1$ group; and
$R^1$ represents —A—Ar, —A—Z—Ar, —CO—Ar, or —$SO_2$—Ar, in which A represents an alkylene group having 1 to 8 carbon atoms selected from methylene, ethylene, trimethylene, tetramethylene, pentamethylene, hexamethylene, heptamethylene and octmethylene or an alkylene group having 1 to 8 carbon atoms which is substituted by a straight or branched chain alkyl group having 1 to 5 carbon atoms selected from methylmethylene, propylene, methyltrimethylene, dimethylethylene, dimethyltetramethylene, ethylethylene and dimethyltrimethylene; Z represents carbon, oxygen, sulfur or nitrogen; Ar represents a phenyl group, a pyridyl group, a naphthyl group, a pyrimidyl group, or a quinolyl group, each of which may be unsubstituted or substituted by one to five substituents selected from hydrogen; a halogen selected from fluoro, chloro, bromo and iodo; a hydroxy group; a carboxylic acid group; an alkyl group having 1 to 10 carbon atoms selected from methyl, ethyl, n-propyl, isopropyl, n-butyl, isobutyl, tert-butyl, n-pentyl, isopentyl, 1-methybutyl, n-hexyl, 1-methylpentyl, n-heptyl, 4-methylhexyl, 1-ethylpentyl, 1,4-dimethylpentyl, n-octyl, 6-methylheptyl and 2-ethylhexyl; an alkenyl group having 1 to 10 carbon atoms selected from vinyl, allyl, 3-pentenyl and 1-hexenyl; an alkynyl group having 1 to 10 carbon atoms; a haloalkyl group having 1 to 10 carbon atoms selected from fluoromethyl, chloromethyl, bromomethyl, iodomethyl, trifluoromethyl, trifluoroethyl, trifluoropropyl, trifluoromethylethyl and trifluoromethylpropyl; an alkoxy group having 1 to 10 carbon atoms selected from methoxy, ethoxy, n-propoxy, isopropoxy, n-butoxy, isobutoxy, tert-butoxy, n-pentyloxy, isopentyloxy, n-hexyloxy, n-heptyloxy, 1-propylbutoxy, n-octyloxy, 5-methylhexyloxy, 2-ethylhexyloxy and 1,6-dimethylhexyloxy; an alkenyloxy group having 1 to 10 carbon atoms; an alkynyloxy group having 1 to 10 carbon atoms; a haloalkoxy group having 1 to 10 carbon atoms; a phenyl group; a phenoxy group; an aralkyl group selected from benzyl, 1-phenylethyl, 2-phenylethyl, 3-phenylpropyl and 4-phenylbutyl; an aralkyloxy group selected from benzyloxy, 2-phenylethoxy, 3-phenylpropoxy and 4-phenylbutoxy; a substituted phenyl group selected from 2-chlorophenyl, 2-bromophenyl, 2-fluorophenyl, 2-iodophenyl, 3-fluorophenyl, 2,3-dichlorophenyl, 4-hydroxyphenyl, 2-methylphenyl, 4-methylphenyl, 3-ethylphenyl, 4-propylphenyl, 4-isopropylphenyl, 4-butylphenyl, 4-tert-butylphenyl, 4-pentylphenyl, 2,4-dimethylphenyl, 2-trifluoromethylphenyl, 3-trifluoromethylphenyl, 2-methoxyphenyl, 4-methoxyphenyl, 3-ethoxyphenyl, 2-propoxyphenyl, 4-butoxyphenyl and 2,4-dimethoxyphenyl; a substituted phenoxy group selected from 3,4,5-trimethoxyphenoxy, 2-chlorophenoxy, 2,3-dichlorophenoxy, 4-hydroxyphenoxy, 2-methoxyphenoxy, 4-butylphenoxy and 2,4-dimethylphenoxy; a substituted aralkyl group selected from chlorobenzyl, bromobenzyl, fluorobenzyl, iodobenzyl, dichlorobenzyl, dibromobenzyl, difluorobenzyl, hydroxybenzyl, methylbenzyl, halomethylbenzyl, methoxybenzyl and trimethoxybenzyl; a substituted aralkyloxy group selected from chlorobenzyloxy, dimethylbenzyloxy, trifluoromethylbenzyloxy and trimethoxybenzyloxy; —$COR^4$; —$CONR^4R^5$; —$CO_2R^4$; —$NHCOR^4$; N(OH)H; —N(OH)$COR^4$; —$CH_2OR^4$; —$OCH_2CO_2R^4$; —$CH_2SR^4$; —$CH_2NR^4R^5$; —$SR^4$; —$OSR^4$; —$SO_2NR^4R^5$; —$NR^4R^5$; —$NR^4SO_2R^4$, in which $R^4$ and $R^5$ are the same or different and each is hydrogen, an alkyl group having 1 to 10 carbon atoms or a cycloalkyl group having 3 to 10 carbon atoms; —$SCX_3$, in which X represents halogen; —CN; —$NO_2$; or cyclic linked substituent, —Z—A—Z'—, in which Z and A are as defined above, and Z' represents carbon, oxygen, sulfur or nitrogen, selected from —$OCH_2O$—, —$OCH_2CH_2O$—, —$OCH_2CH_2CH_2O$—, —$OCH_2CH_2N$—, —$NCH_2CH_2N$—, —$OCH_2CH_2$—, —$NCH_2CH_2$—, —$NCH_2CH_2CH_2SCH_2S$—, —$SCH_2CH_2S$—, —$SCH_2$—, —$SCH_2CH_2$—and —$SCH_2CH_2CH_2$—.

15. A compound according to claim 13, wherein
$R^2$ is hydrogen; and

R¹ is —CH₂—Ar, —CH₂CH₂—Ar, —CH₂CH₂CH₂—Ar, CH₂O—Ar, —CH₂CH₂CH₂—O—Ar,

or —SO₂—Ar, in which Ar is a phenyl group, a pyridyl group, a pyrimidyl group or a quinolyl group, each of which is unsubstituted or substituted by one to five substituents selected from the group consisting of hydrogen, halogen, a hydroxy group, an alkyl group having 1 to 10 carbon atoms, a haloalkyl group having 1 to 10 carbon atoms, an alkoxy group having 1 to 10 carbon atoms, a haloalkoxy group having 1 to 10 carbon atoms, a phenyl group, a phenoxy group, an aralkyl group, an aralkyloxy group,

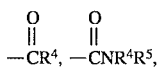

—CO₂R⁴, —CH₂OR⁴, —NR⁴R⁵, —CH₂NR⁴R⁵, —CN, —NO₂ and —Z—A—Z'—.

16. A compound according to claim 13, wherein said compound is selected from the group consisting of
10-benzyloxy-Ginkgolide B,
10-(2',4'-dichlorobenzyloxy)-Ginkgolide B,
10-(4'-chlorobenzyloxy)-Ginkgolide B,
10-(4'-methoxybenzyloxy)-Ginkgolide B,
10-(3',4',5'-trimethoxybenzyloxy)-Ginkgolide B,
10-(2'-methylbenzyloxy)-Ginkgolide B,
1,10-bis(2'-methylbenzyloxy)-Ginkgolide B,
10-(4'-methylbenzyloxy)-Ginkgolide B,
10-(3'-phenoxypropoxy)-Ginkgolide B,
10-(2'-phenylethoxy)-Ginkgolide B,
10-(3',4',5'-trimethoxybenzoyloxy)-Ginkgolide B,
10-(4'-phenylbenzyloxy)-Ginkgolide B,
10-piperonyloxy-Ginkgolide B,
10-(2',3',4',5',6'-pentafluorobenzyloxy)-Ginkgolide B,
10-(2',4'-difluorobenzyloxy)-Ginkgolide B,
10-(4'-fluorobenzyloxy)-Ginkgolide B,
10-(2'-fluorobenzyloxy)-Ginkgolide B,
10-benzoyloxy-Ginkgolide B,
1-benzoyloxy-Ginkgolide B,
1,10-bis(2',4'-dichlorobenzyloxy)-Ginkgolide B,
10-(3'-trifluoromethylbenzyloxy)-Ginkgolide B,
10-benzenesulfonyloxy-Ginkgolide B,
10-(3'-methoxybenzyloxy)-Ginkgolide B,
10-(4'-trifluoromethylbenzyloxy)-Ginkgolide B,
1,10-bis(4'-trifluoromethylbenzyloxy)-Ginkgolide B,
10-(4'-hydroxybenzyloxy)-Ginkgolide B,
10-(4'-ethoxybenzyloxy)-Ginkgolide B,
10-(3'-bromobenzyloxy)-Ginkgolide B,
10-(4'-iodobenzyloxy)-Ginkgolide B,
10-(2',3',4'-trihydroxybenzyloxy)-Ginkgolide B,
10-(2'-iodobenzyloxy)-Ginkgolide B,
10-(2'-hydroxybenzyloxy)-Ginkgolide B,
10-(3'-iodobenzyloxy)-Ginkgolide B,
10-(3'-hydroxybenzyloxy)-Ginkgolide B,
10-(2'-bromobenzyloxy)-Ginkgolide B,
10-(3',4'-dihydroxybenzyloxy)-Ginkgolide B,
10-(4'-bromobenzyloxy)-Ginkgolide B,
10-(2'-chlorobenzyloxy)-Ginkgolide B,
10-(3'-chlorobenzyloxy)-Ginkgolide B,
10-(2',4'-dibromobenzyloxy)-Ginkgolide B,
10-(2',3',4',5',6'-pentachlorobenzyloxy)-Ginkgolide B,
10-(2',3',4',5',6'-pentabromobenzyloxy)-Ginkgolide B,
10-(2',3',4',5',6'-pentaiodobenzyloxy)-Ginkgolide B,
10-(2'-methoxybenzyloxy)-Ginkgolide B,
10-(3'-methoxybenzyloxy)-Ginkgolide B,
10-(2'-ethoxybenzyloxy)-Ginkgolide B,
10-(3'-ethoxybenzyloxy)-Ginkgolide B,
10-(2'-propoxybenzyloxy)-Ginkgolide B,
10-(3'-propoxybenzyloxy)-Ginkgolide B,
10-(4'-propoxybenzyloxy)-Ginkgolide B,
10-(2'-isopropoxybenzyloxy)-Ginkgolide B,
10-(3'-isopropoxybenzyloxy)-Ginkgolide B,
10-(4'-isopropoxybenzyloxy)-Ginkgolide B,
10-(4'-methylbenzyloxy)-Ginkgolide B,
10-(2'-ethylbenzyloxy)-Ginkgolide B,
10-(3'-ethylbenzyloxy)-Ginkgolide B,
10-(4'-ethylbenzyloxy)-Ginkgolide B,
10-(2'-propylbenzyloxy)-Ginkgolide B,
10-(3'-propylbenzyloxy)-Ginkgolide B,
10-(2'-bromoethoxy)-Ginkgolide B,
10-(2'-iodoethoxy)-Ginkgolide B,
10-(3,5-dimethyl-2-pyridinyl)-methoxy-Ginkgolide B,
10-(4-methoxy-3,5-dimethyl-2-pyridinyl)-methoxy-Ginkgolide B,
10-(3,5-dimethyl-4-nitro-2-pyridinyl)-methoxy-Ginkgolide B,
10-(2-pyridinyl)-methoxy-Ginkgolide B,
10-(5-butyl-2-pyridinyl)-methoxy-Ginkgolide B,
10-(2-pyridinyl)-ethoxy-Ginkgolide B,
10-(2-quinolinyl)-methoxy-Ginkgolide B,
10(3,5-dimethyl-4-amino-2-pyridinyl)-methoxy-Ginkgolide B,
10-(3,5-dimethyl-4-nitro-2-pyridinyl)-methoxy-Ginkgolide B,
10-(3,5-dimethyl-4-hydroxy-2-pyridinyl)-methoxy-Ginkgolide B,
10-(3,5-dimethyl-4-hydroxyamino-2-pyridinyl)-methoxy-Ginkgolide B,
10-(4-benzoylamino-3,5-dimethyl-2-pyridinyl)-methoxy-Ginkgolide B,
10-(4-N-benzoyl-N-hydroxyamino-3,5-dimethyl-2-pyridinyl)-methoxy Ginkgolide B,
10-(6-chloro-3-pyridinyl)-methoxy-Ginkgolide B,
10-(3-pyridinyl)-methoxy-Ginkgolide B,
10-(4-pyridinyl)-methoxy-Ginkgolide B,
10-(2-(4-ethoxypyridinyl))-methoxy-Ginkgolide B,
10-(2-(4-nitropyridinyl)))-methoxy-Ginkgolide B,
10-(2-(6-methyl-3-propoxypyridinyl))-methoxy-Ginkgolide B,
10-(2-(4-hydroxyaminopyridinyl)))-methoxy-Ginkgolide B,
10-(2-(5-methoxyethoxymethoxypyridinyl))-methoxy-Ginkgolide B,
10-(2-(5-hydroxypyridinyl)))-methoxy-Ginkgolide B,
10-(4'-propylbenzyloxy)-Ginkgolide B,
10-(2'-isopropylbenzyloxy)-Ginkgolide B,
10-(3'-isopropylbenzyloxy)-Ginkgolide B,
10-(4'-isopropylbenzyloxy)-Ginkgolide B,
10-(2'-butylbenzyloxy)-Ginkgolide B,
10-(3'-butylbenzyloxy)-Ginkgolide B,
10-(4'-butylbenzyloxy)-Ginkgolide B,
10-(4'-pentylbenzyloxy)-Ginkgolide B,
10-(2',3'-dihydroxybenzyloxy)-Ginkgolide B,
10-(2',4'-dihydroxybenzyloxy)-Ginkgolide B,
10-(2',5'-dihydroxybenzyloxy)-Ginkgolide B,
10-(2',6'-dihydroxybenzyloxy)-Ginkgolide B,
10-(3',5'-dihydroxybenzyloxy)-Ginkgolide B,
10-(3',6'-dihydroxybenzyloxy)-Ginkgolide B,
10-(3',4',5'-trihydroxybenzyloxy)-Ginkgolide B,
10-(2'-vinylbenzyloxy)-Ginkgolide B,
10-(3'-vinylbenzyloxy)-Ginkgolide B, 10-(4'-vinylbenzyloxy)-Ginkgolide B,
10-(2'-allylbenzyloxy)-Ginkgolide B,
10-(2'-trifluoromethylbenzyloxy)-Ginkgolide B,
10-(2'-trichloromethylbenzyloxy)-Ginkgolide B,
10-(3'-trichloromethylbenzyloxy)-Ginkgolide B,
10-(4'-trichloromethylbenzyloxy)-Ginkgolide B,
10-(2'-tribromomethylbenzyloxy)-Ginkgolide B,
10-(3'-tribromomethylbenzyloxy)-Ginkgolide B,
10-(4'-tribromomethylbenzyloxy)-Ginkgolide B,
10-(2'-fluoromethylbenzyloxy)-Ginkgolide B,
10-(3'-allylbenzyloxy)-Ginkgolide B,
10-(4'-allylbenzyloxy)-Ginkgolide B,
10-(3'-fluoromethylbenzyloxy)-Ginkgolide B,
10-(4'-fluoromethylbenzyloxy)-Ginkgolide B,
10-(2'-chloromethylbenzyloxy)-Ginkgolide B,
10-(3'-chloromethylbenzyloxy)-Ginkgolide B,
10-(4'-chloromethylbenzyloxy)-Ginkgolide B,
10-(2'-bromomethylbenzyloxy)-Ginkgolide B,
10-(3'-bromomethylbenzyloxy)-Ginkgolide B,
10-(4'-bromomethylbenzyloxy)-Ginkgolide B,
10-(2'-fluoromethoxybenzyloxy)-Ginkgolide B,
10-(3'-fluoromethoxybenzyloxy)-Ginkgolide B,
10-(4'-fluoromethoxybenzyloxy)-Ginkgolide B,
10-(2'-chloromethoxybenzyloxy)-Ginkgolide B,
10-(3'-chloromethoxybenzyloxy)-Ginkgolide B,
10-(4'-chloromethoxybenzyloxy)-Ginkgolide B,
10-(2'-bromomethoxybenzyloxy)-Ginkgolide B,
10-(3'-bromomethoxybenzyloxy)-Ginkgolide B,
10-(4'-bromomethoxybenzyloxy)-Ginkgolide B,
10-(2'-trifluoromethoxybenzyloxy)-Ginkgolide B,
10-(3'-trifluoromethoxybenzyloxy)-Ginkgolide B,
10-(4'-trifluoromethoxybenzyloxy)-Ginkgolide B,
10-(2'-trichloromethoxybenzyloxy)-Ginkgolide B,
10-(3'-trichloromethoxybenzyloxy)-Ginkgolide B,
10-(4'-trichloromethoxybenzyloxy)-Ginkgolide B,
10-(2'-tribromomethoxybenzyloxy)-Ginkgolide B,
10-(3'-tribromomethoxybenzyloxy)-Ginkgolide B,
10-(4'-tribromomethoxybenzyloxy)-Ginkgolide B,
10-(2'-phenoxybenzyloxy)-Ginkgolide B,
10-(2'-benzylbenzyloxy)-Ginkgolide B,
10-(3'-phenoxybenzyloxy)-Ginkgolide B,
10-(3'-benzylbenzyloxy)-Ginkgolide B,
10-(4'-phenoxybenzyloxy)-Ginkgolide B,
10-(4'-benzylbenzyloxy)-Ginkgolide B,
10-(1'-phenethoxy)-Ginkgolide B,
10-(3'-phenpropoxy)-Ginkgolide B,
10-(4'-phenbutoxy)-Ginkgolide B,
10-(4'-(2"-phenethyl)-benzyloxy)-Ginkgolide B,
10-(4'-(1"-phenethyl)-benzyloxy)-Ginkgolide B,
10-(4'-(3"-phenpropyl)-benzyloxy)-Ginkgolide B,
10-(4'-(4"-phenbutyl)-benzyloxy)-Ginkgolide B,
10-(4-(2"-chlorophenyl)-benzyloxy)-Ginkgolide B,
10-(4'-(2"-bromophenyl)-benzyloxy)-Ginkgolide B,
10-(4'-(2"-fluorophenyl)-benzyloxy)-Ginkgolide B,
10-(4'-(2"-bromophenyl)-benzyloxy)-Ginkgolide B,
10-(4'-(2"-iodophenyl)-benzyloxy)-Ginkgolide B,
10-(4'-(3"-fluorophenyl)-benzyloxy)-Ginkgolide B,
10-(4'-(2",3"-dichlorophenyl)-benzyloxy)-Ginkgolide B,
10-(4'-(4"-hydroxyphenyl)-benzyloxy)-Ginkgolide B,
10-(4'-(2"-methylphenyl)-benzyloxy)-Ginkgolide B,
10-(4'-(4"-methylphenyl)-benzyloxy)-Ginkgolide B,
10-(4'-(3"-ethylphenyl)-benzyloxy)-Ginkgolide B,
10-(4'-(4"-propylphenyl)-benzyloxy)-Ginkgolide B,
10-(4'-(4"-isopropylphenyl)-benzyloxy)-Ginkgolide B,
10-(4'-(4"-butylphenyl)-benzyloxy)-Ginkgolide B,
10-(4'-(4"-pentylphenyl)-benzyloxy)-Ginkgolide B,
10-(4'-(2",4"-dimethylphenyl)-benzyloxy)-Ginkgolide B,
10-(4'-(2"-trifluoromethylphenyl)-benzyloxy)-Ginkgolide B,
10-(4'-(2"-methoxyphenyl)-benzyloxy)-Ginkgolide B,
10-(4'-(3"-methoxyphenyl)-benzyloxy)-Ginkgolide B,
10-(4'-(4"-methoxyphenyl)-benzyloxy)-Ginkgolide B,
10-(4'-(3"-ethoxyphenyl)-benzyloxy)-Ginkgolide B,
10-(4'-(2"-propoxyphenyl)-benzyloxy)-Ginkgolide B,
10-(4'-(4"-butoxyphenyl)-benzyloxy)-Ginkgolide B,
10-(4'-(2",4"-dimethoxyphenyl)-benzyloxy)-Ginkgolide B,
10-(4'-(3",4",5"-trimethoxyphenoxy)-benzyloxy)-Ginkgolide B,
10-(4'-(2"-chlorophenoxy)-benzyloxy)-Ginkgolide B,
10-(4'-(2",3"-dichlorophenoxy)-benzyloxy)-Ginkgolide B,
10-(4'-(4"-hydroxyphenoxy)-benzyloxy)-Ginkgolide B,
10-(4'-(2"-methoxyphenoxy)-benzyloxy)-Ginkgolide B,
10-(4'-(4"-butylphenoxy)-benzyloxy)-Ginkgolide B,
10-(4'-(2",4"-dimethylphenoxy)-benzyloxy)-Ginkgolide B,
10-(4'-(4"-chlorobenzyl)-benzyloxy)-Ginkgolide B,
10-(4'-(4"-bromobenzyl)-benzyloxy)-Ginkgolide B,
10-(4'-(4"-fluorobenzyl)-benzyloxy)-Ginkgolide B,
10-(2'-nitrobenzyloxy)-Ginkgolide B,
10-(3'-nitrobenzyloxy)-Ginkgolide B,
10-(4'-nitrobenzyloxy)-Ginkgolide B,
10-(2'-cyanobenzyloxy)-Ginkgolide B,
10-(3'-cyanobenzyloxy)-Ginkgolide B,
10-(4'-cyanobenzyloxy)-Ginkgolide B,
10-(2'-aminobenzyloxy)-Ginkgolide B,
10-(3'-aminobenzyloxy)-Ginkgolide B,
10-(4'-aminobenzyloxy)-Ginkgolide B,
10-(2'-dimethylaminobenzyloxy)-Ginkgolide B,
10-(3'-dimethylaminobenzyloxy)-Ginkgolide B,
10-(4'-dimethylaminobenzyloxy)-Ginkgolide B,
10-(3',4'-dihydroxybenzyloxy)-Ginkgolide B,
10-(3,5-dimethyl-4-hydroxybenzyloxy)-Ginkgolide B,
10-(3,5-di-tert-butyl-4-hydroxybenzyloxy)-Ginkgolide B,
10-(4-hydroxy-3-methoxybenzyloxy)-Ginkgolide B,
10-(3,5-dimethoxy-4-hydroxybenzyloxy)-Ginkgolide B and
10-(3-amino-4-hydroxy-5-methyl-benzyloxy)-Ginkgolide B.

17. A pharmaceutical composition comprising a compound of formula (I) as claimed in claim 13 and a pharmaceutically acceptable carrier.

18. A pharmaceutical composition for the prevention on or treatment of PAF-induced diseases or allergen-induced diseases comprising a compound of formula (I) as claimed in claim 13.

19. A method for treating asthma in a mammal which comprises administering to the mammal an antiasthmatic amount of a compound as claimed in claim 13.

20. A method for treating anaphylatic and septic shock in a mammal which comprises administering to said mammal an effective amount of a compound as claimed in claim 13.

21. A method for treating psoriasis in a mammal which comprises administering to the mammal an effective amount of a compound as claimed in claim 13.

22. A method for treating bowel necrosis in a mammal which comprises administering to the mammal an effective amount of a compound as claimed in claim 13.

23. A method for treating adult respiratory distress syndrome in a mammal which comprises administering to the mammal an effective amount of a compound as claimed in claim 13.

24. A method for treating transplant rejection in a mammal which comprises administering to the mammal an effective amount of a compound as claimed in claim 13.

* * * * *

UNITED STATES PATENT AND TRADEMARK OFFICE
CERTIFICATE OF CORRECTION

PATENT NO. : 5,541,183
DATED : July 30, 1996
INVENTOR(S) : PARK et al.

Page 1 of 2

It is certified that error appears in the above-indentified patent and that said Letters Patent is hereby corrected as shown below:

Claim 1, column 39, line 19, "-A-Het," should read -- -A-Het. --; and column 39, line 40, delete the second occurrence of "-COR$^4$,".

Claim 2, column 39, line 57, "-A-Het," should read -- -A-Het. --.

Claim 3, column 41, line 6, "R$_2$" should read --R$^2$--;

column 41, line 22, "anaralkyloxy" should read --an aralkyloxy--.

Claim 4, column 42, line 12, "10-(2'-propoxybenzyloxy)-Ginkgolide B" should read --10-(3'-propoxybenzyloxy)-Ginkgolide B--;

column 42, line 26, "10-(2'-(1"-morphorinyl)-ethyl)-Ginkgolide B" should read --10-(2'-(1"-morphorinyl)-ethoxy)-Ginkgolide B--; and

UNITED STATES PATENT AND TRADEMARK OFFICE
CERTIFICATE OF CORRECTION

PATENT NO. : 5,541,183
DATED : July 30, 1996
INVENTOR(S) : PARK et al.

It is certified that error appears in the above-indentified patent and that said Letters Patent is hereby corrected as shown below:

column 43, line 23, "10-(4'-allylbenxyloxy)-Ginkgolide B" should read

--10-(4'-allybenzyloxy)-Ginkgolide B--.

Claim 14, column 45, line 63, "octmethylene" should read --octamethylene--.

Claim 16, column 49, line 52, "10-(4-(2"-chlorophenyl)-benzyloxy)-Ginkgolide B"

should read --10-(4'-2"-chlorophenyl)-benzyloxy)-Ginkgolide B--.

Signed and Sealed this

Twenty-ninth Day of October 1996

Attest:

BRUCE LEHMAN

Attesting Officer  Commissioner of Patents and Trademarks